United States Patent
Greene et al.

(10) Patent No.: US 9,557,307 B2
(45) Date of Patent: Jan. 31, 2017

(54) BEVERAGE DIAGNOSTIC AND PRESERVATION DEVICES AND METHODS

(71) Applicant: Sommatic, LLC, Atlanta, GA (US)

(72) Inventors: Russell W. Greene, Atlanta, GA (US);
Daniel B. Lipton, Atlanta, GA (US);
David J. Trettin, Atlanta, GA (US);
Trent J. Kahute, Atlanta, GA (US);
James H. Wood, San Antonio, TX (US); Jerome A. Helffrich, San Antonio, TX (US); David J. Postell, San Antonio, TX (US); Bob Vanecek, San Antonio, TX (US)

( * ) Notice: Subject to any disclaimer, the term of this patent is extended or adjusted under 35 U.S.C. 154(b) by 0 days.

(21) Appl. No.: 14/748,124

(22) Filed: Jun. 23, 2015

(65) Prior Publication Data

US 2015/0293067 A1 Oct. 15, 2015

Related U.S. Application Data

(63) Continuation-in-part of application No. 14/272,495, filed on May 7, 2014.
(Continued)

(51) Int. Cl.
*G01N 33/18* (2006.01)
*G01N 33/00* (2006.01)
(Continued)

(52) U.S. Cl.
CPC .......... *G01N 33/0042* (2013.01); *G01N 21/61* (2013.01); *G01N 33/146* (2013.01);
(Continued)

(58) Field of Classification Search
CPC .............. G01N 33/146; G01N 33/0042; G01N 33/0065; G01N 21/31; G01N 21/80; G01N 21/25; G01N 21/51; G01N 21/64; G01N 2021/3155
(Continued)

(56) References Cited

U.S. PATENT DOCUMENTS 4,490,042 A 12/1984 Wyatt
5,200,909 A 4/1993 Juergens
(Continued)

FOREIGN PATENT DOCUMENTS

WO WO 0233404 A2 * 4/2002 ........... G01N 33/146

OTHER PUBLICATIONS

Ribereau-Gayon et al. "Handbook of Enology Volume 1 The Microbiology of Wine and Vinifications $2^{nd}$ Edition". 2006. <https://vinumvine.files.wordpress.com/2011/08/pascal-ribereau-gayon-denis-dubourdieu-bernard-doneche-aline-lonvaud-handbook-of-enology-volume-1-the-microbiology-of-wine-and-vinifications-2nd-edition.pdf>.*
(Continued)

*Primary Examiner* — Lisa Caputo
*Assistant Examiner* — Jonathan Dunlap

(57) ABSTRACT

An apparatus for determining freshness of wine stored in a container includes a housing, a gas sensor, an optical sensor pair, and electrical circuitry. The gas sensor is affixed to the housing such that it extends into a headspace of the container above the wine. The optical sensor pair is positioned such that the optical sensor pair extends into the headspace above the wine. The electrical circuitry is contained in the housing and is electrically interfaced to the gas sensor and to the optical sensor pair. The electrical circuitry operates the gas sensor to generate a series of gas level measurements and operates the optical sensor pair to generate a series of optical transmission measurements. A quality parameter corresponding to the freshness of the wine is determined based on
(Continued)

both the series of gas level measurements and the series of optical transmission measurements.

25 Claims, 34 Drawing Sheets

Related U.S. Application Data

(60) Provisional application No. 61/902,561, filed on Nov. 11, 2013, provisional application No. 61/867,236, filed on Aug. 19, 2013, provisional application No. 61/820,429, filed on May 7, 2013.

(51) Int. Cl.
    *G01N 33/14* (2006.01)
    *G01N 21/61* (2006.01)
    *G01N 21/64* (2006.01)
    *G01N 21/51* (2006.01)
    *G01N 21/25* (2006.01)
    *G01N 21/31* (2006.01)
    *G01N 21/80* (2006.01)

(52) U.S. Cl.
    CPC ............ *G01N 21/25* (2013.01); *G01N 21/31* (2013.01); *G01N 21/51* (2013.01); *G01N 21/64* (2013.01); *G01N 21/80* (2013.01); *G01N 33/0065* (2013.01); *G01N 2021/3155* (2013.01)

(58) Field of Classification Search
USPC ... 73/19.01, 19.02, 19.1; 436/164, 167, 168, 436/171
See application file for complete search history.

(56) References Cited

U.S. PATENT DOCUMENTS

| | | | |
|---|---|---|---|
| 5,239,180 A | 8/1993 | Clarke | |
| 5,716,850 A | 2/1998 | Takhar et al. | |
| 5,770,038 A | 6/1998 | Iwama et al. | |
| 5,844,123 A * | 12/1998 | Marsh ................ | G01N 33/0042 73/19.12 |
| 6,462,546 B1 | 10/2002 | Schmalbein et al. | |
| 6,489,774 B1 | 12/2002 | van de Goor et al. | |
| 6,541,260 B1 | 4/2003 | Pariseau et al. | |
| 6,576,474 B2 | 6/2003 | Wallach | |
| 6,723,285 B2 | 4/2004 | Chen et al. | |
| 7,288,768 B2 | 10/2007 | Gore et al. | |
| 7,339,377 B2 | 3/2008 | Augustine et al. | |
| 7,394,262 B2 | 7/2008 | Manneschi | |
| 7,906,975 B2 | 3/2011 | Federici et al. | |
| 7,971,470 B2 | 7/2011 | Broz | |
| 8,030,948 B2 | 10/2011 | Manneschi | |
| 8,237,452 B2 | 8/2012 | Federici et al. | |
| 8,449,824 B2 | 5/2013 | Sun | |
| 8,519,726 B2 | 8/2013 | Sun | |
| 9,212,993 B2 * | 12/2015 | Thomsen ............... | G01N 21/59 |
| 2003/0178323 A1 | 9/2003 | Fiedler et al. | |
| 2004/0000653 A1 * | 1/2004 | Nordlund ............... | G01N 21/31 250/573 |
| 2004/0147036 A1 | 7/2004 | Krenn et al. | |
| 2004/0148107 A1 | 7/2004 | Piotrowski et al. | |
| 2004/0161366 A1 | 8/2004 | Miller | |
| 2008/0227215 A1 * | 9/2008 | Voipio .................... | G01N 21/80 436/164 |
| 2008/0268547 A1 | 10/2008 | Avent et al. | |
| 2009/0215646 A1 | 8/2009 | Anslyn et al. | |
| 2009/0321646 A1 | 12/2009 | Cozzolino | |
| 2010/0091279 A1 * | 4/2010 | Juhl ...................... | G01N 33/146 356/326 |
| 2010/0112680 A1 | 5/2010 | Brockwell et al. | |
| 2011/0050431 A1 | 3/2011 | Hood et al. | |
| 2011/0053283 A1 | 3/2011 | Hood et al. | |
| 2013/0199266 A1 | 8/2013 | Maranon | |
| 2013/0203171 A1 | 8/2013 | Sportsman | |
| 2013/0236976 A1 | 9/2013 | Thomsen | |
| 2014/0096590 A1 | 4/2014 | Amin et al. | |

OTHER PUBLICATIONS

Berna, Metal Oxide Sensors for Electronic Noses and Their Application to Food Analysis, Apr. 15, 2010, Sensors 2010, vol. 10, pp. 3882-3910, Basel, Switzerland.

Lozano et al., Identification of Typical Aroma of Red Wines with Thin Film Sensors Combined with Pattern Recognition Techniques, 2005 Spanish Conference on Electron Devices, Feb. 2, 2004, pp. 549-552, IEEE, Madrid, Spain.

Mamat et al., An Electronic Nose for Reliable Measurement and Correct Classification of Beverages, Sensors 2011, Jun. 17, 2011, pp. 6435-6453, vol. 11, Basel, Switzerland.

Peris et al., A 21st Century Technique for Food Control: Electronic Noses, 2009, Analytica Chimica Acta, vol. 638, pp. 1-15, Valencia, Spain.

Vaskova, Spectroscopic Determination of Methanol Content in Alcoholic Drinks, International Journal of Biology and Biomedical Engineering, 2014, pp. 27-34, vol. 8.

\* cited by examiner

| Gas Chromatograph - Chemiluminescence Detector | | | Concentration (ppm) DL >5ppm | | Concentration (%w/v) (ng/μL) | |
|---|---|---|---|---|---|---|
| Sample | liquid/gas | vol inj (μL) | H2S | SO2 | H2S | SO2 |
| Red wine bottle † | gas | 1000 | | 5.79 | | 5.79 |
| Red wine bottle † | liquid | 0 | 3.34 | 26.48 | < 5 | |
| White wine bottle † | gas | 1000 | | 8.76 | | 8.76 |
| White wine bottle † | liquid | 0 | 2.96 | 26.34 | < 5 | 13.17 |
| Day 1: 13:45 | gas | 1000 | | | | |
| Day 1: 13:45 | liquid | 0 | 2.74 | 20.36 | < 5 | 10.18 |
| Day 1: 16:40 | gas | 1000 | | 2.13 | | < 5 |
| Day 1: 16:40 | liquid | 0 | 2.74 | 19.68 | < 5 | 9.84 |
| Day 3: 12:26 | gas | 1000 | | 2.05 | | < 5 |
| Day 3: 12:26 | liquid | 0 | 2.79 | 16.74 | < 5 | 8.37 |
| Day 4: 11:00 | gas | 1000 | | 3.18 | | < 5 |
| Day 4: 11:00 | liquid | 0 | 2.72 | 13.85 | < 5 | 6.93 |
| Day 4: 15:40 | gas | 1000 | | 2.51 | | < 5 |
| Day 4: 15:40 | liquid | 0 | 2.75 | 12.41 | < 5 | 6.21 |
| Day 4: 16:45 | gas | 1000 | | 2.83 | | < 5 |
| Day 4: 16:45 | liquid | 0 | 2.74 | 12.56 | < 5 | 6.28 |
| Day 4 10:20 | gas | 1000 | | 2.68 | | < 5 |
| Day 5: 10:20 | liquid | 0 | 2.67 | 8.96 | < 5 | < 5 |
| Day 5: 13:58 | gas | 1000 | | 2.51 | | < 5 |
| Day 5: 13:58 | liquid | 0 | 2.52 | 7.05 | < 5 | < 5 |
| Day 5: 17:00 | gas | 1000 | | | | |
| Day 5: 17:00 | liquid | 0 | 2.61 | 5.36 | < 5 | < 5 |
| Day 6: 10:25 | gas | 1000 | 2.05 | 2.40 | < 5 | < 5 |
| Day 6: 10:25 | liquid | 0 | 2.72 | 5.06 | < 5 | < 5 |
| Day 6: 14:25 | gas | 1000 | | 2.42 | | < 5 |
| Day 6: 14:25 | liquid | 0 | 2.73 | 3.13 | < 5 | < 5 |

FIG. 37

BEVERAGE DIAGNOSTIC AND PRESERVATION DEVICES AND METHODS

CROSS-REFERENCE TO RELATED APPLICATIONS

This application is a continuation-in-part of U.S. patent application Ser. No. 14/272,495, filed May 7, 2014, which claims the benefit of U.S. Provisional Patent Application No. 61/820,429, filed May 7, 2013, U.S. Provisional Patent Application No. 61/867,236, filed Aug. 19, 2013, and U.S. Provisional Patent Application No. 61/902,561, filed Nov. 11, 2013, each of which is hereby incorporated by reference in its entirety.

FIELD OF THE INVENTION

This disclosure relates in general to beverage diagnostic and preservation devices. In particular, this disclosure describes apparatuses and methods for determining and monitoring freshness of wine stored in a container.

BACKGROUND

Wine typically diminishes in quality and freshness relatively quickly after a bottle is initially opened. The quality and freshness of wine in an opened bottle may begin decreasing within several hours of the bottle being opened and may continue to decrease to an unacceptable level within several days. Many factors may contribute to how quickly an opened bottle of wine degrades. These factors can include storage conditions, number of times the bottle is opened, how quickly the bottle is resealed, the initial quality of the wine, the type of wine, the age of the wine, and the pH of the wine, as well as other factors, including combinations thereof. Because there are potentially multiple factors that can contribute to the degradation of the wine, it can be difficult to precisely predict when an opened bottle of wine has progressed to an unacceptable level of freshness or quality because a simple measure of time since the bottle has been opened may be insufficient in some circumstances.

In bars, restaurants, and other commercial establishments that serve wine, monitoring wine quality may be a particular challenge due to the relatively large number of open bottles that may be on hand and the period of time that may pass between successive servings from each open bottle. Due to the cost of wine, establishments cannot afford to prematurely discard opened bottles due to mere suspicion that a wine may no longer be good. At the same time, serving wine that has degraded beyond a good or acceptable level can also have negative impacts on the establishment due to customer dissatisfaction and/or impacts on reputation. Consequently, there is a need for improved methods of determining and monitoring freshness of wine stored in a container.

SUMMARY

Apparatuses and methods for determining and monitoring freshness of wine stored in a container are provided. In particular, the apparatuses and methods are applicable to wine containers that have been opened. An exemplary apparatus includes a housing, a gas sensor, an optical sensor pair, and electrical circuitry. The housing is removably attachable to the wine container such that it spans an opening of the container and seals the opening of the container when the housing is attached to the container.

The gas sensor is affixed to the housing such that it extends into a headspace of the container above the wine when the housing is attached to the container. The optical sensor pair includes an optical emitter and an optical detector. The sensor pair is positioned to extend into the headspace above the wine when the housing is attached to the container. The optical emitter and optical detector are positioned such that optical energy emitted from the optical emitter is transmitted through at least a portion of the headspace toward the optical detector. The electrical circuitry is contained in the housing and is electrically interfaced to the gas sensor and to the optical sensor pair. The electrical circuitry operates the gas sensor to generate a series of gas level measurements each indicating a measured level of a gas in the headspace. The electrical circuitry also operates the optical sensor pair to generate a series of optical transmission measurements each indicating a level of optical transmission of the emitted optical energy through the headspace. A quality parameter corresponding to the freshness of the wine is determined based on both the series of gas level measurements and the series of optical transmission measurements.

Other embodiments of the techniques disclosed herein may include other apparatuses, methods, systems, and/or a computer-processor readable storage medium having non-transitory computer processor-executable instructions for implementing one or more of the techniques disclosed herein.

While multiple embodiments are disclosed, still other embodiments will become apparent to those skilled in the art from the following detailed description, which shows and describes illustrative embodiments. As will be realized, the disclosed embodiments are susceptible to modifications in various aspects, all without departing from the scope of the present disclosure. Accordingly, the figures and the detailed description are to be regarded as illustrative in nature and not restrictive.

BRIEF DESCRIPTION OF THE DRAWINGS

FIG. 37 illustrates test results for an experiment in which sulfur dioxide and hydrogen sulfide was measured in a bottle of red wine and a bottle of white wine using a gas chromatograph detector with chemiluminescence detector.

DETAILED DESCRIPTION

Figure 1:
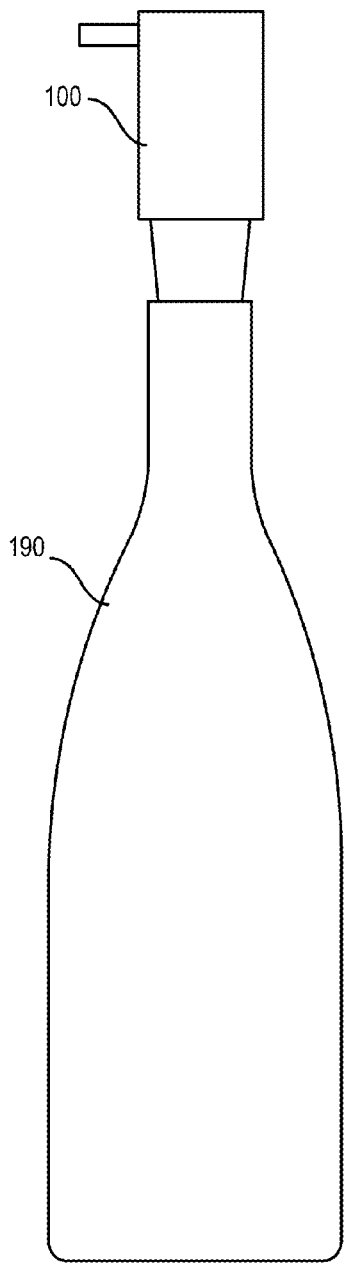
FIG. 1 is a side view of a beverage diagnostic device, according to an exemplary embodiment.

Wine in an opened bottle decreases in quality after its initial opening. Wine may begin to noticeably decrease in freshness or quality within several hours of the bottle being opened and may continue to decrease to an unacceptable quality level within several days. However, it is difficult to predict exactly when an opened bottle of wine has degraded to a point of being unacceptable because many factors may contribute to how quickly it degrades. Consequently, it can be difficult to precisely determine when an opened bottle of wine has progressed to an unacceptable level of freshness or quality because a simple measure of time since the bottle has been opened may not be sufficient. Improved apparatuses, methods, systems, and/or computer-executable instructions for determining and monitoring freshness of wine stored in a container are provided.

Commercial establishments that serve wine by the glass and stock a relatively large number of opened bottles of wine may wish to monitor the freshness and quality of the opened bottles in order to avoid discarding partial bottles prematurely while also not serving customers wine which has dropped below an acceptable quality level. It is desirable for these establishments to have a relatively easy, relatively low cost method of determining quality of and monitoring open bottles of wine, particularly doing so on an ongoing basis in an automated fashion. In addition, people enjoying wine in their own home may wish to preserve an opened bottle of wine for several days while not waiting too long to finish the remaining portion. In either case, improved diagnostic and monitoring devices are desired. It may also be desirable for a monitoring device to remain affixed to each open bottle such that minimal effort is required to check the quality of the bottle and such that the bottle does not have to be opened or disturbed to make a quality determination.

Sulfur dioxide ($SO_2$) is commonly added to wines to improve freshness and shelf life. Although it is naturally produced in small amounts by wine yeast during the process of alcoholic fermentation, most of the sulfur dioxide present in wines has been added during the winemaking or bottling process. Sulfur dioxide commonly plays two roles in the preservation of wine. First, sulfur dioxide is an anti-microbial agent that helps curtail growth of undesirable, fault producing yeasts and bacteria. Second, sulfur dioxide is an antioxidant that safeguards the wine's integrity and protects it against browning. Measuring changes in the sulfur dioxide levels and/or other gases in the headspace of an opened bottle of wine over time can provide a good indicator of the freshness and/or quality of the wine.

Compact and relatively low cost sulfur dioxide gas sensors lend themselves to the types of headspace measurements described herein. However, these types of sensors can be sensitive to various environmental conditions and sometimes provide somewhat unstable readings due to a variety of factors. Because wine bottles may be stored, handled, and served under a variety of conditions, measurements from a sulfur dioxide sensor may be temporarily adversely affected. In addition, differing chemistries of different wines may lead to varying results as well. Some sensors or measurements may not be stable under certain conditions or may be temporarily affected by other factors that are not necessarily indicative of wine quality. Consequently, it is beneficial to use at least a secondary quality or freshness measurement in conjunction with measurements from a sulfur dioxide sensor. While some of the examples herein involve making measurements in or through a fluid, it may also be beneficial to make measurements only within the headspace of the wine in order to avoid contaminating the wine, in order to avoid the need for components that are fluid resistant, and in order to avoid additional cleaning processes when switching a diagnostic device among bottles of wine.

An exemplary apparatus includes a housing and a gas sensor. The housing is removably attachable to the container such that it spans the opening of a wine bottle. The gas sensor is affixed to the housing such that it extends into the headspace of the bottle above the wine when the housing is attached to the bottle. In order to address some or all of the issues discussed above, the apparatus also includes an optical sensor pair for making optical measurements that further provide information regarding gas levels in the headspace. The optical sensor pair includes an optical emitter and an optical detector. The optical sensor pair is positioned such that it extends into the headspace above the wine when the housing is attached to the bottle. The optical emitter and optical detector are positioned such that optical energy emitted from the optical emitter is transmitted through at least a portion of the headspace toward and into the optical detector.

The apparatus may also contain electrical circuitry that is contained in the housing and is electrically interfaced to the gas sensor and to the optical sensor pair. The electrical circuitry operates the gas sensor to generate a series of gas level measurements each indicating a measured level of a gas in the headspace. The series of gas level measurements include gas level measurements made over a period of time. The electrical circuitry also operates the optical sensor pair to generate a series of optical transmission measurements each indicating a level of optical transmission of the emitted optical energy through the portion of the headspace. The series of optical transmission measurements includes optical level measurements made over a period of time. A quality parameter corresponding to the freshness of the wine is determined based on both the series of gas level measurements and the series of optical transmission measurements. The quality parameter is monitored over a period of time to monitor the freshness of the wine.

Determining the quality parameter based on both of the series of measurements lends stability and reliability to the determination in case one or the other of the measurements is unstable or provides temporarily inaccurate or unreliable measurements. In one example, the gas sensor may be somewhat unstable when disturbed, when initially inserted into the bottle, and/or when exposed to varying conditions, such as temperature. Rather than immediately indicating a poor wine quality in response to this instability, the gas sensor measurements may be further considered in light of the optical transmission measurements. In one example, the wine may be designated as bad or spoiled only if both the gas sensor measurement and the optical transmission measurements indicate that the wine is bad. In another example, the wine may be designated as bad or spoiled if one of the measurement indicates that the wine is bad and the other measurement indicates that the wine is marginal or bad. In yet another example, the wine may be designated as good if one of the measurements indicates that the wine is good even though the other measurement indicates that wine may be bad.

Other combinational uses of the gas and optical measurements are possible. In one other example, only one of the measurements may be used when the other is outside of an expected range. In yet another example, only one of the measurements may be used for a period of time after the device has been powered, inserted into the bottle, and/or physically moved in order to allow one or more other sensors or measurements to stabilize.

In addition, the determination of the quality parameter for the wine may be based on an average of one or both of the measurements over a period of time. In other words, the wine may not be indicated to be good or bad based on a single measurement from one or both of the sensors, and may only be determined to be good or bad based on an average or other mathematical amalgamation of readings over a period of time in order to minimize the effects of temporarily inaccurate readings, flawed readings, and/or false readings.

In some configurations, the apparatus may be implemented in the form of a cap or plug that plugs the opening of a wine bottle. In other configurations, the apparatus may be implemented in the form of a spout that performs one or more of the measurement and monitoring functions described herein, as well as allows pouring of wine from the bottle without removal of the apparatus from the bottle.

In one exemplary embodiment, illustrated in FIG. 1, a beverage diagnostic device 100 is coupled to a beverage container 190, such as a wine bottle, in which wine or any fluid may be stored. The device may include a body, the body having a lower portion, an upper portion, and a fluid chamber formed therein. In one embodiment, the lower portion of the device is coupled to an upper portion of a wine bottle using a press fit. In one embodiment, an outside diameter of the lower portion of the device is smaller than an inside diameter of the upper portion of the wine bottle.

Figure 2:
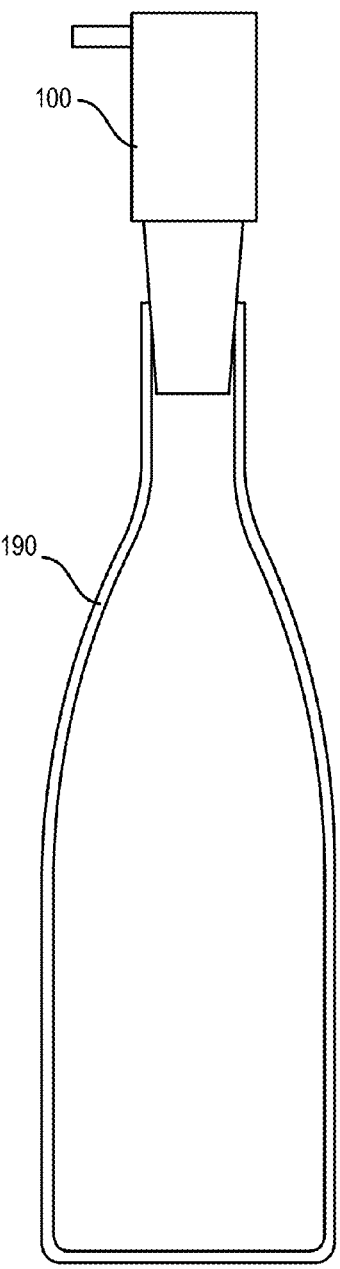
FIGS. 2-4 are side sectional views of the beverage diagnostic device of FIG. 1.

FIG. 2 illustrates a side sectional view of beverage diagnostic device 100 inserted into container 190.

In one embodiment, the lower portion of the device is formed from a rubber material, plastic material, or any other type of material suitable for pressing into a neck of an opened bottle. A fluid chamber in the device may include a fluid passage extending from the lower portion of the device to a spout located on the upper portion of the device. In one embodiment, the fluid passage allows fluid to flow from the container, through the lower portion of the device and out of the device.

In some configurations, a wine monitoring device may include a timer, a digital timer, a mechanical timer, an electrical timer, or any combination thereof. In one example, coupling the device to the container activates the timer such that the timer begins recording a first time in order to determine a duration of time. In another embodiment, the device includes a timer activator. The timer activator may be in contact with the inner diameter of the container and detect the coupling of the device to the container. The timer activator may activate the timer.

A timer may measure a first time period beginning when the device is coupled to the container. In one embodiment, the device may include a timer display so that the first time is displayed to a user. The timer display may be located on the upper portion of the device. The timer display may also have a digital screen displaying a digital counter. In one embodiment, the first time extends from installation of the device into the container until the device is removed or detached from the container. The timer activator may detect the removal or decoupling of the device from the container. In one variation, upon the timer activator's detection of the removal or decoupling of the device from the container, the timer's first time is set to zero. Coupling the device to a second container may begin the recording of a second period of time, similar to the first time.

The device may be coupled to the container to record the freshness of any fluid within the container. For example, after opening a bottle of wine, the device may be coupled to the bottle of wine, with the timer displaying how long the timer has been coupled to the bottle of wine. That is, the freshness of any wine contained in the container may correlate to the period of time that has passed since the bottle of wine has been opened. When the device is coupled to the wine bottle directly after it is opened, the freshness of the wine is measured by the timer. As discussed previously, determining freshness of wine based on time alone may not provide ideal results under all conditions. Consequently, the timer and timing features described herein may also be used in conjunction with any of the other wine quality measurements or techniques described herein.

Figure 3:
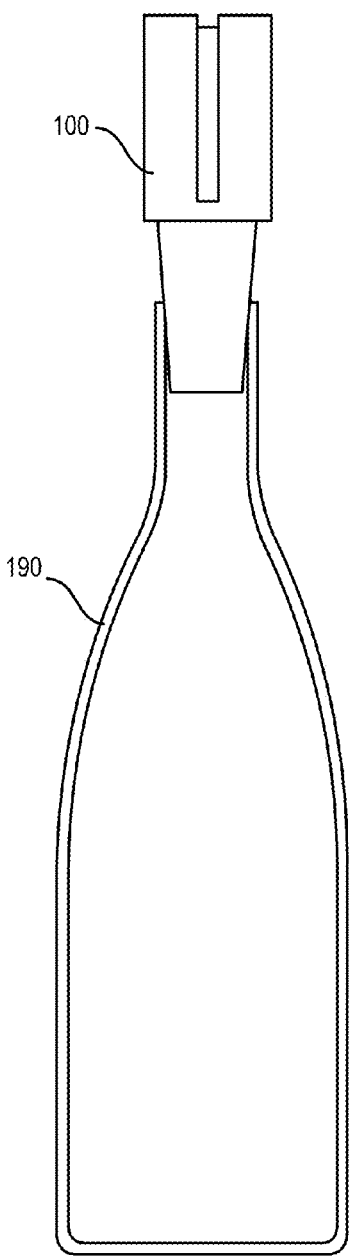
Figure 4:
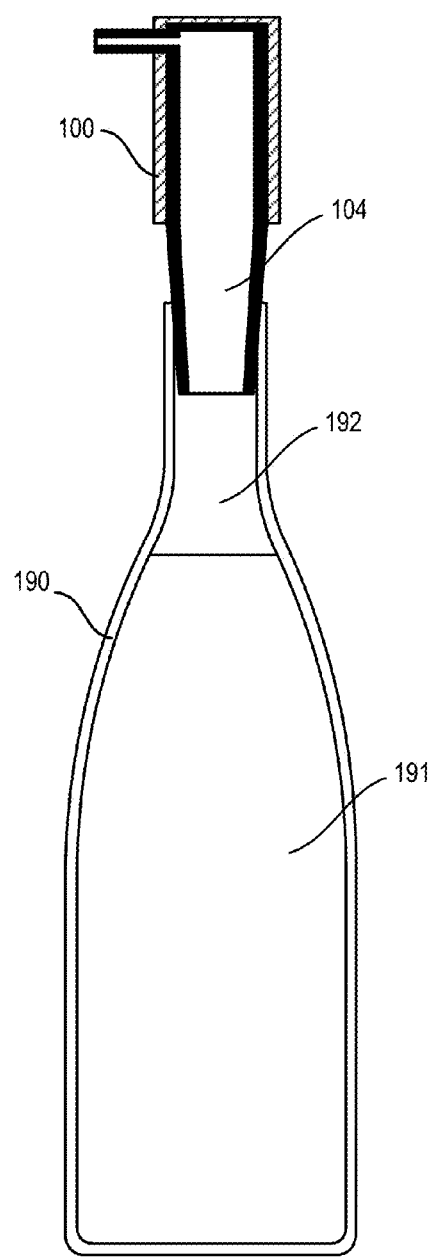

FIGS. 3 and 4 further illustrate side sectional views of beverage diagnostic device 100 inserted into container 190. FIG. 4 further illustrates wine 191 in container 190 with headspace 192 in container 190 above wine 191. FIG. 4 further illustrates bore 104 through beverage diagnostic device 100, which permits wine 191 to be poured through beverage diagnostic device 100.

Figure 5:
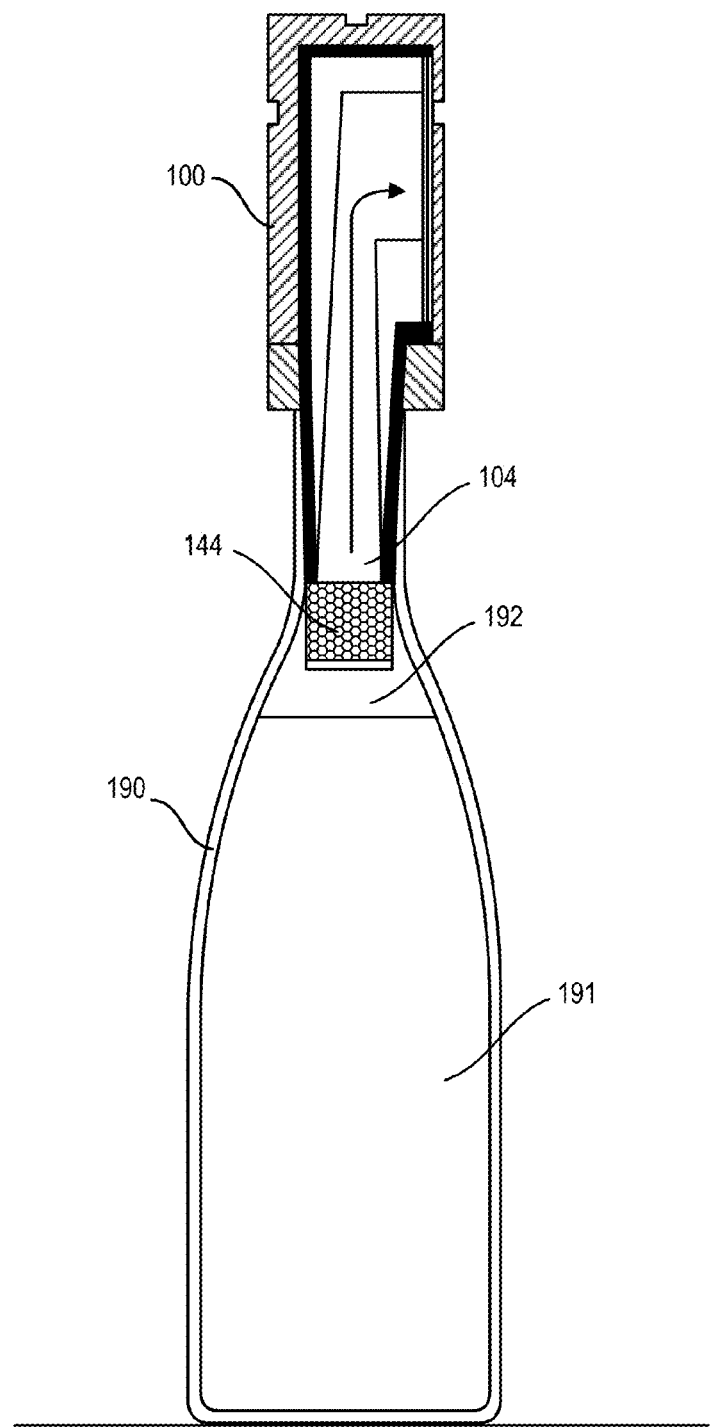
FIG. 5 is a side sectional view of a beverage diagnostic device in a closed position, according to another exemplary embodiment.
Figure 6:
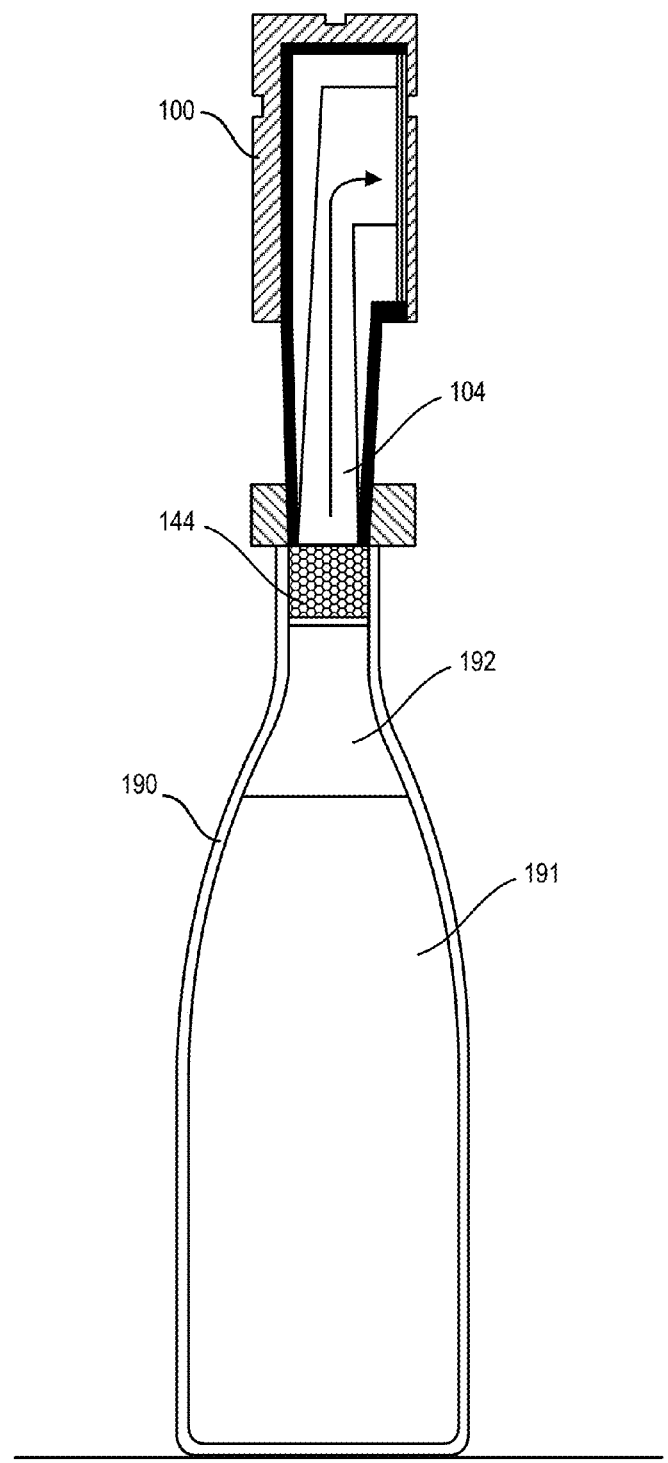
FIG. 6 is a side sectional view of the beverage diagnostic device of FIG. 5 in an open position.

In another exemplary embodiment, illustrated in FIGS. 5 and 6, a beverage diagnostic device 100 has a freshness sensor that measures the activity of the (solvated) hydrogen ions and/or the hydrogen ion concentration (pH). The freshness sensor may include an element that measures the pH of the fluid stored in the container. The freshness sensor may include a pH strip. In one embodiment, the element can measure the pH of the fluid stored in the container by contacting vapors, fumes, or chemicals emanating from the fluid, or by contacting the fluid itself. As illustrated in FIG. 5, the device may include a band located above the lower portion of the device. The band may be configured to couple to an outer diameter of the upper portion of the wine bottle. The lower portion of the device may move relative to the band to transition diagnostic device 100 between an opened position and a closed position. In an exemplary embodiment, diagnostic device 100 may include a filter that is coupled to the lower portion of the device.

Figure 7:
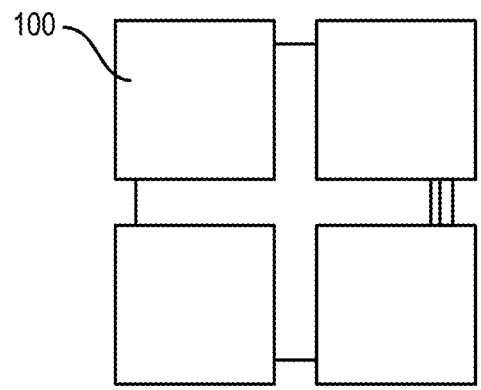
FIG. 7 is a top view of the beverage diagnostic device of FIG. 5.
Figure 8:
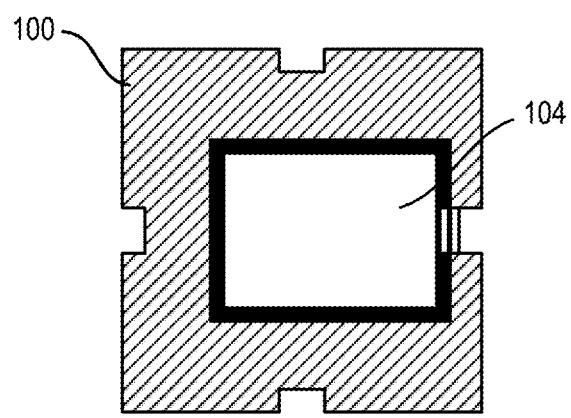
FIG. 8 is a top sectional view of the beverage diagnostic device of FIG. 5.
Figure 9:
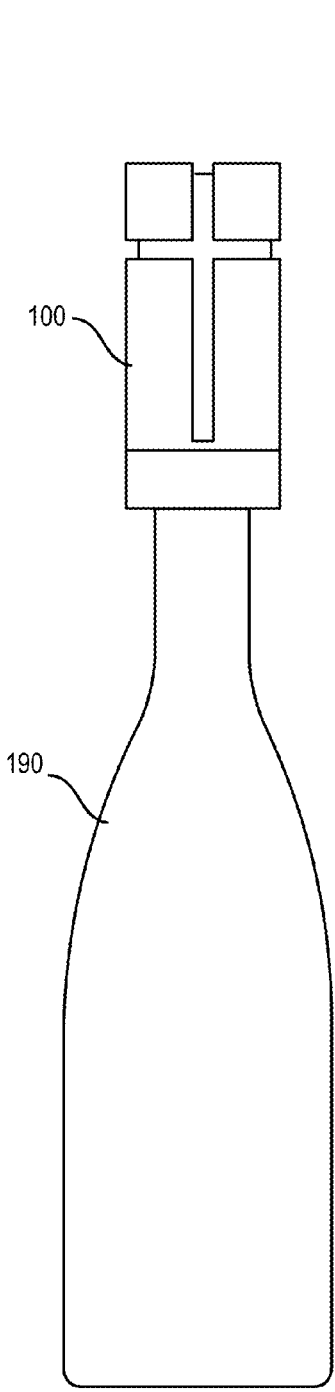
FIG. 9 is a side view of the beverage diagnostic device of FIG. 5 in a closed position.
Figure 10:
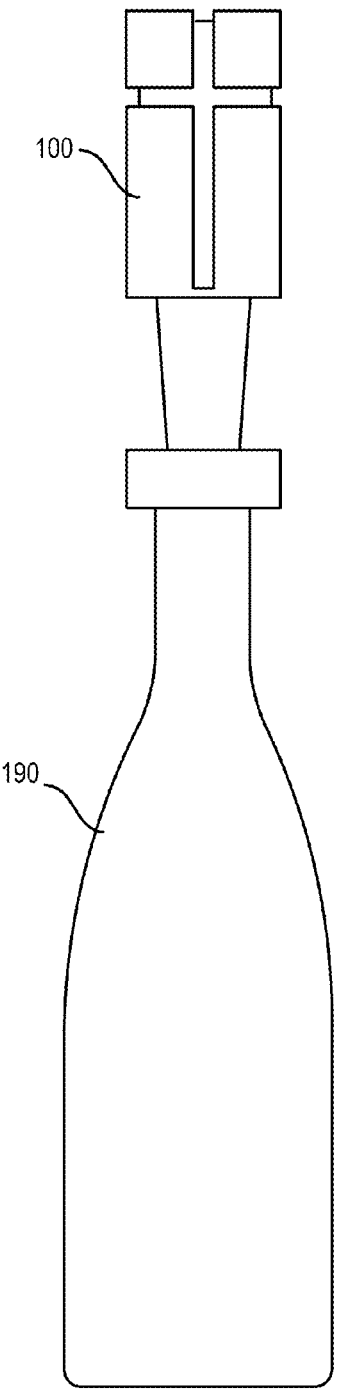
FIG. 10 is another side view of the beverage diagnostic device of FIG. 5 in an open position.

FIG. 7 is a top view of beverage diagnostic device 100. FIG. 8 is a top sectional view of beverage diagnostic device 100. FIG. 9 is a side view of beverage diagnostic device 100 in the closed position. FIG. 10 is a side view of beverage diagnostic device 100 in the opened position.

Figure 11:
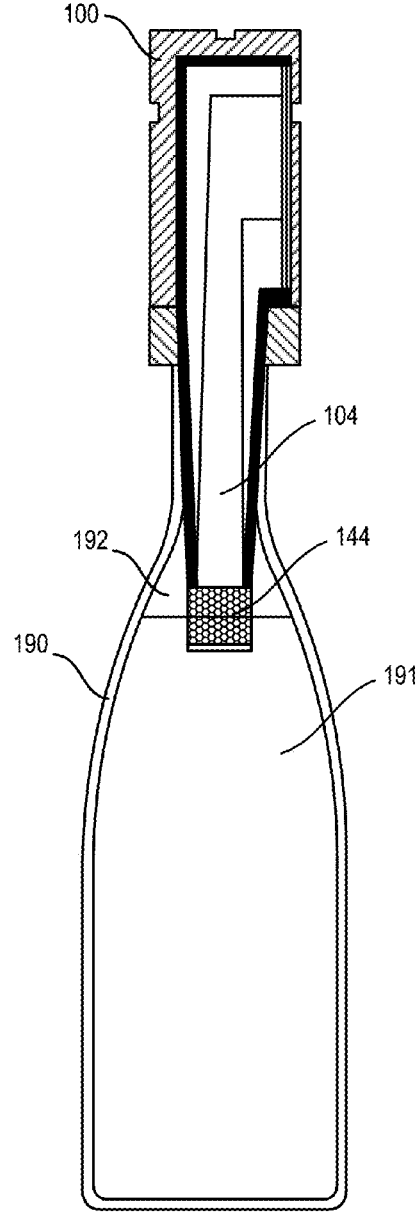
FIGS. 11 and 12 are additional side sectional views of the beverage diagnostic device of FIG. 5.
Figure 12:
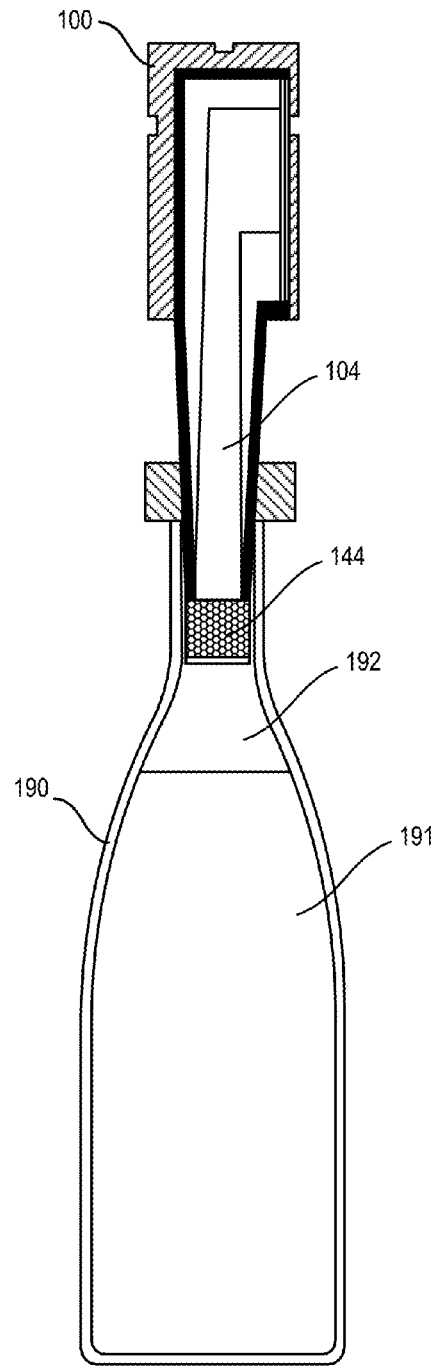
Figure 13:
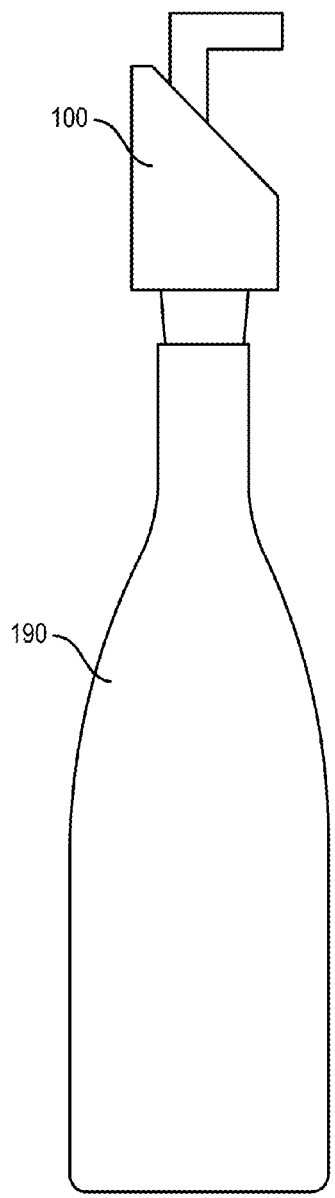
FIG. 13 is a side view of a beverage diagnostic device, according to another exemplary embodiment.
Figure 14:
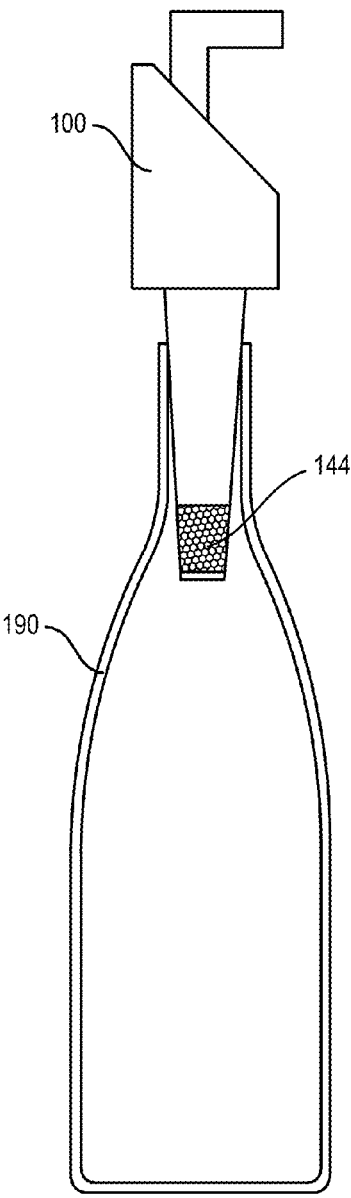
FIG. 14 is a side sectional view of the beverage diagnostic device of FIG. 13.
Figure 15:
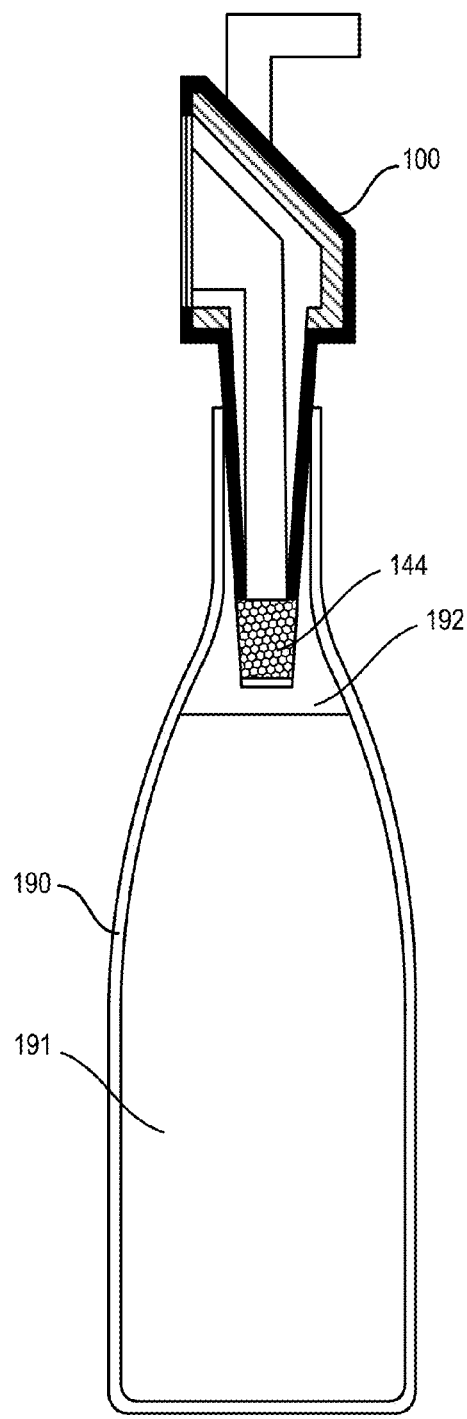
FIG. 15 is a side sectional view of the beverage diagnostic device of FIG. 13 in an open position.
Figure 16:
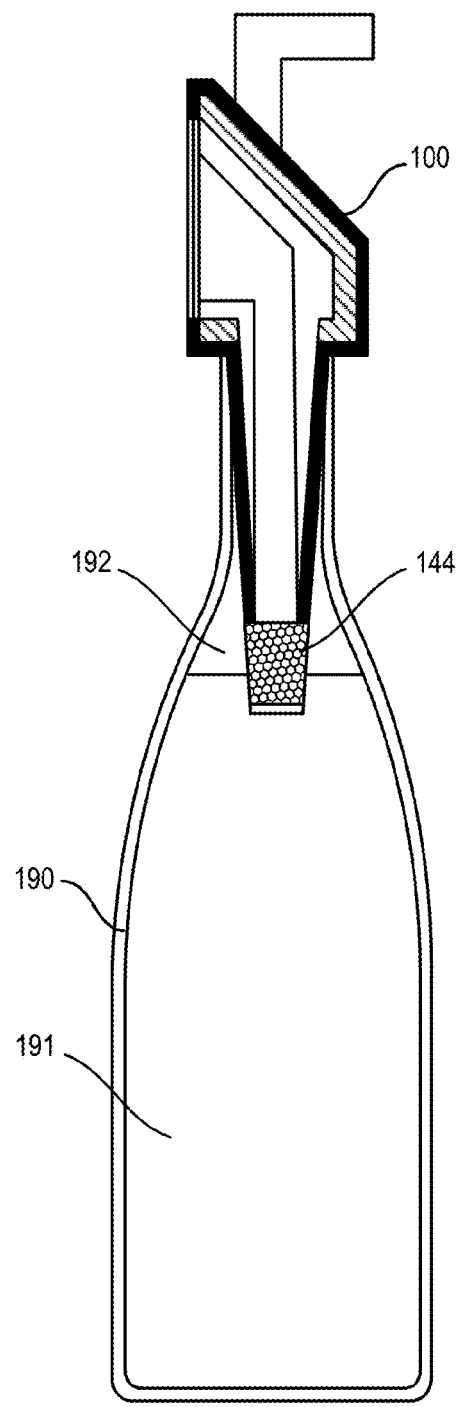
FIG. 16 is a side sectional view of the beverage diagnostic device of FIG. 13 in a closed position.
Figure 17:
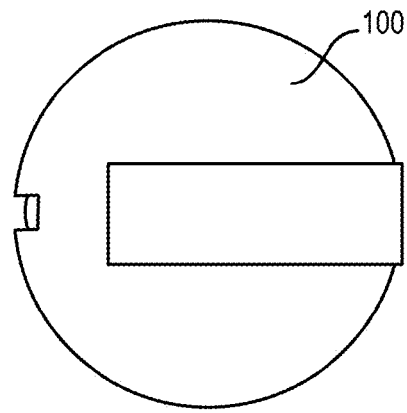
FIG. 17 is a top view of the beverage diagnostic device of FIG. 13.
Figure 18:
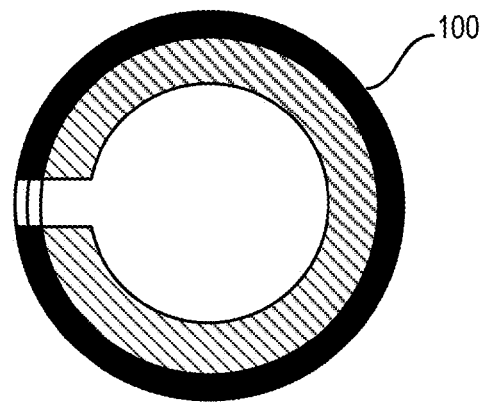
FIG. 18 is a top sectional view of the beverage diagnostic device of FIG. 13.

FIGS. 11 and 12 illustrate side sectional views of beverage diagnostic device 100 including a filter 144. Filter 144 may contact the fluid when the device is in the closed position. In one embodiment, vapor or fumes are forced through the filter and into the fluid chamber when the device transitions between the opened and closed positions. In one embodiment, fluid is drawn into the filter when the device is in the closed position. For example, the fluid could be drawn into the filter due to a wicking force or due to a capillary action associated with the filter. As discussed in further detail below, one or more other types of filters or membranes may be included to shield one or more of the sensors from liquid and/or vapor.

In one variation, the fluid chamber forms a contact chamber in the upper portion of the device. A freshness measuring or detection element may be coupled to an inner surface of the contact chamber. A pocket or opening may be formed in the contact chamber of the device such that a freshness indicator that is placed in the opening is visible to a user. In some cases, changing the position of the device, from the opened position to the closed position, creates a vacuum within the container and/or seals the container such that the freshness of the fluid within the container is preserved or such that the rate of spoliation of the fluid is reduced. In some embodiments, the device preserves the freshness of the fluid by preventing oxygen from entering the container.

In one example, the diagnostic device may be coupled to the filter such that a pH measurement made by or at the filter is displayed as the freshness parameter or is used in determining the freshness parameter in conjunction with one or more of the other measurement techniques discussed herein. In another example, a measuring element may be located in the contact chamber. In some configurations, a measuring element may be a pH test strip placed in an opening or pocket. The element may measure the pH of the fluid when the vapor or fumes from the fluid are forced through the filter and into the contact chamber.

In some configurations, a pH measurement may be displayed on the device using one or more of text, an icon, a symbol, an illuminated indictor, and/or a multicolored indicator. For example, the device might display a green color if the pH of the wine is within a first range, a purple color if the pH of the wine is within a second range, and a red color if the pH of the wine is within a third range. In one embodiment, the color green is displayed when the wine is most fresh, the color purple is displayed when there is roughly 3-4 days of shelf life left, and the color red is displayed when the wine is likely to be spoiled or otherwise below an acceptable quality or freshness level.

In some embodiments, the device detects a beverage's freshness, provides an indication of freshness, and/or provides an indication of an estimated remaining period of time that the beverage will likely be fresh. In another embodiment, freshness of a beverage is determined through the monitoring and/or detection of freshness factors including oxidation levels, sulfur containing compounds, sulfur dioxide, and/or the beverage's overall "volatile acidity," as determined by the device.

FIGS. 13-18 illustrate various views of beverage diagnostic device 100 with the band omitted from the device. The opened position of the device may be associated with a first length of the device passing through an opening of the container and the closed position may be associated with a second length of the device passing through the opening of the container, wherein the second length is greater than the first length. The container may be shaken, tipped, or otherwise moved so that fluid stored within the container, or vapor emanating from the fluid, comes into contact with one or more sensors used to determine freshness. In other examples, fluid or vapor contact is not necessary.

The techniques disclosed herein may also be implemented as methods. In one exemplary embodiment, a method of determining freshness of a fluid stored within a container includes coupling a beverage diagnostic device to the container and using one or more freshness sensors to measure the freshness of the fluid stored within the container in accordance with any of the techniques, or variations of the techniques, disclosed herein.

Figure 19:
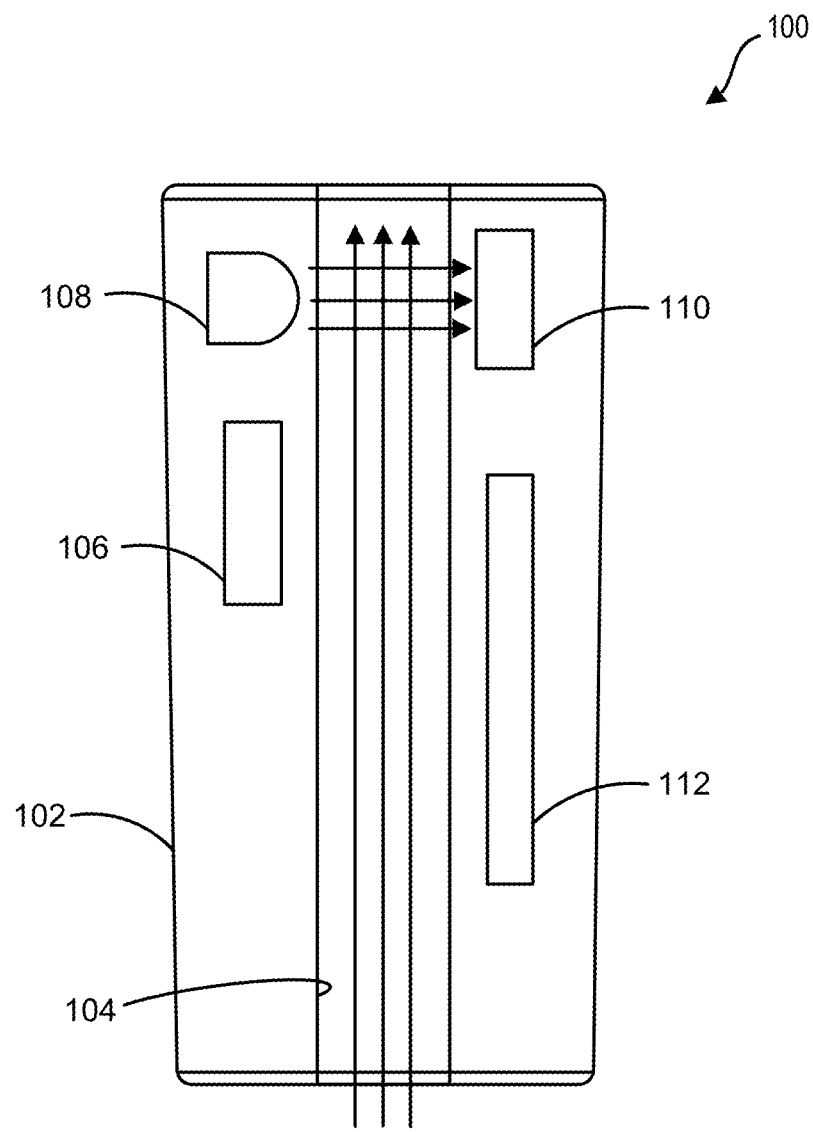
FIG. 19 is a diagrammatic illustration of a beverage diagnostic device according to an exemplary embodiment.

FIG. 19 is a diagrammatic illustration of beverage diagnostic device 100. Beverage diagnostic device 100 includes a stopper or body member 102, at least a lower portion of which is adapted to be disposed in, or connected to, a wine bottle. In one embodiment, at least the lower portion of body member 102 is adapted to be inserted through the mouth of a wine bottle and to extend within the neck of the wine bottle. A longitudinally extending bore 104 is formed through body member 102. An electrical power source, such as a battery 106, is attached to or contained in body member 102. An emitter 108, a sensor 110, and an electrical circuit board 112, also sometimes referred to as a printed circuit board (PCB), are also connected to and/or contained in body member 102. Each of the emitter 108, the sensor 110, and electrical circuit board 112 receive electrical power from battery 106, either directly or indirectly.

Electrical circuit board 112 is electrically interfaced to and/or in electrical communication with each of emitter 108 and sensor 110, either directly or indirectly. Emitter 108 and sensor 110 are opposed to one another across bore 104. In an exemplary embodiment, electrical circuit board 112 includes an accelerometer or other sensor for detecting acceleration, movement, or motion, to determine when a bottle has been moved, tipped, or poured. Beverage diagnostic device 100 may also include an indicator or output device, such as a digital display, a liquid crystal display, one or more light emitting diodes (LEDs), one or more lights, one or more alarms, or any combination thereof. The indicators and/or output devices may provide visual feedback, audible feedback, another type of sensory feedback, or any combination thereof.

Figure 20:
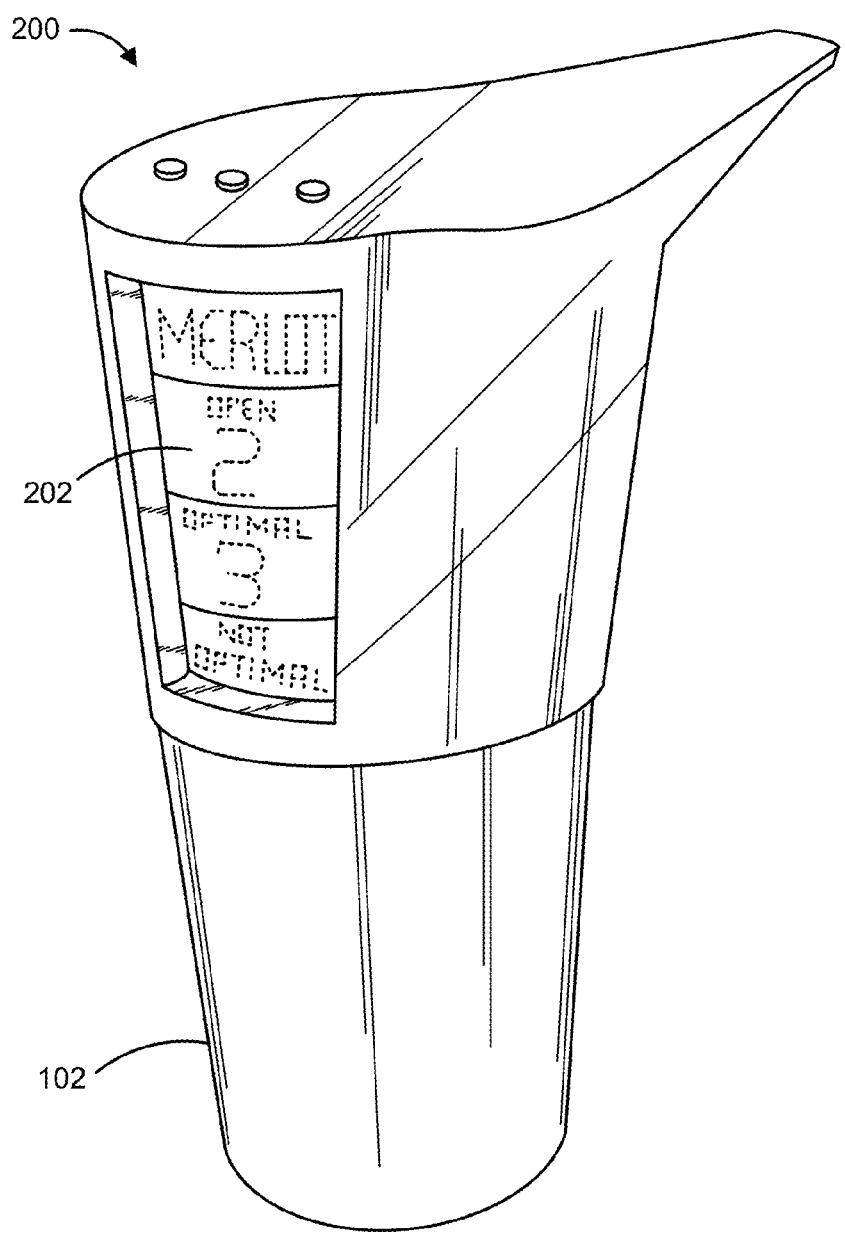
FIG. 20 is a perspective view of a beverage diagnostic device, according to an exemplary embodiment.

FIG. 20 illustrates a perspective view of beverage diagnostic device 200. Beverage diagnostic device 200 includes a display 202 for displaying information relating to the measured freshness or quality of the wine. Display 202 may include a liquid crystal display, LEDs, an e-ink display, another type of display, or a combination thereof. Body member 102 may be inserted into the mouth of a wine bottle that contains a remaining portion of wine such that at least the lower portion of body member 102 extends within the neck of the wine bottle. Beverage diagnostic device 200 may include any of the features, functions, elements, or characteristics of any of the other apparatuses, wine bottle stoppers, and/or beverage diagnostic devices disclosed herein.

After a beverage diagnostic device is coupled to a wine bottle, the wine bottle may be moved and/or rotated so that at least some of the wine flows through a bore. An accelerometer included in the device may detect this movement or rotation of the wine bottle. The beverage diagnostic device, or one or more of the components of the beverage diagnostic device, may be powered on in response to the detection. Once activated, emitter 108 emits a wavelength of light or a variety of wavelengths in a variety of spectral ranges. The reaction or interaction between the light and the flowing wine is detected by sensor 110, which may also be referred to as an optical detector. Sensor 110 sends one or more signals to circuit board 112 for use in determining whether the wine is suitable for consumption or is spoiled. Circuit board 112 sends one or more signals to the indicator or output device, which displays or communicates the state of the wine.

In one embodiment, emitter 108 and sensor 110 are Paired Emitting Detecting Diodes (PEDD). Emitter 108 may include a light emitting diode that emits a specified wavelength. Sensor 110 may include a photodiode positioned opposite emitter 108 across bore 104. During operation, the wavelength of light emitted by emitter 108 reacts with free sulfur dioxide in the wine and the reaction is detected by sensor 110. Sensor 110 sends one or more signals to circuit board 112, which determines the amount of free sulfur dioxide in the wine or a factor corresponding to the amount of free sulfur dioxide in the wine, which is correlated with good or bad wine. In some cases, the optical measurement from the PEDD is combined with or used in conjunction with a measurement from a gas sensor. Circuit board 112 sends one or more signals to the indicator or output device, which displays or communicates the state of the wine.

Free sulfur dioxide in the wine may be used as an indicator to determine whether the wine is good or bad. In an exemplary embodiment, sensor 110 detects the spectral response that correlates to the level of sulfur dioxide present in the wine. Circuit board 112 correlates the spectral response with an oxidation level to determine if the wine is suitable to consume.

In some cases, emitter 108 emits a specified wavelength of light, which is passed through the wine in bore 104. The intensity of the wavelength of light is detected by sensor 110. Sensor 110 sends one or more signals to circuit board 112, which determines whether the detected intensity correlates with good, bad, or marginal wine. Circuit board 112 sends one or more signals to the indicator or output device, which displays or communicates the state of the wine. Light absorbance in the wine can be used as an indicator to determine whether the wine is good, bad, or marginal. Light absorbance may be used in conjunction with one of the other measurement techniques disclosed herein. In some examples, the disclosed methods of determining wine quality or freshness may include a spectrophotometry process.

In another embodiment, during the operation of beverage diagnostic device 100, wine does not flow through bore 104. Instead, the wine bottle remains closed and is flipped over so that wine, which is not being poured, is disposed in bore 104 for measurement purposes.

In some embodiments, instead of, or in addition to an accelerometer on circuit board 112, beverage diagnostic device 100 includes one or more other switches for selectively supplying electrical power to some or all of the electrically powered components described herein. The one or more other switches may include a manual switch, a fluid detector switch, a pressure sensor switch, other types of switches, or any combination thereof.

The disclosed beverage diagnostic apparatuses and devices may also contain one or more controllers, microcontrollers, computer processors, computers, and/or processors, each of which may include or be a part of one or more of the following: a conventional programmable general purpose controller, an application specific integrated circuit (ASIC), a system on a chip (SOC), a programmable logic device, other conventional controller devices, and/or any combination thereof.

In some embodiments, some or all of the elements of the beverage diagnostic devices disclosed herein may be integrated in or included in a container. In other words, a wine bottle or other container may include, or be integral with, one or more of the disclosed embodiments of beverage diagnostic devices, or components thereof.

Any of the devices and apparatuses disclosed herein may also display other information related to a bottle of wine to which is attached including a type of the wine, a vintage of the wine, a description of the wine, a reference code, a date opened, and/or a date or time the bottle was last served from.

Figure 21:
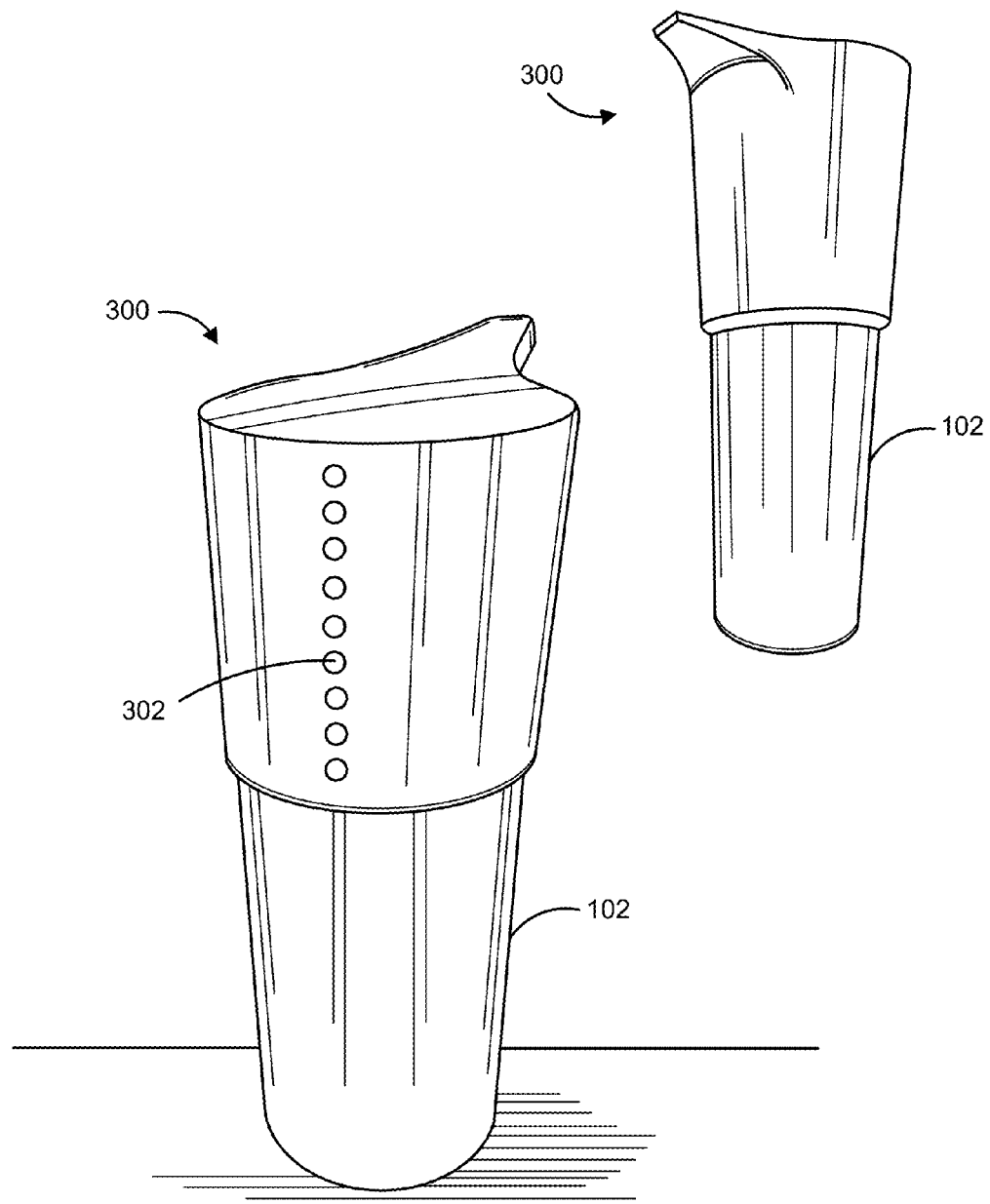
FIG. 21 includes perspective views of a beverage diagnostic device, according to another exemplary embodiment.

FIG. 21 illustrates perspective views of a beverage diagnostic device 300. Beverage diagnostic device 300 may include any of the features, functions, elements, or characteristics of any of the other apparatuses, wine bottle stoppers, and/or beverage diagnostic devices disclosed herein. Beverage diagnostic device 300 includes an indicator or output device in the form of an array of lights 302, which displays or communicates the measured state of the wine in a bottle in which beverage diagnostic device 300 is inserted. Any number of lights or indicators may be included. A subset of the lights 302 are illuminated, activated, and or changed to a selected color to reflect the measured state of the wine.

In an exemplary embodiment, a method of diagnosing the state of wine includes detecting that free sulfur dioxide has been consumed in the wine. In an exemplary embodiment, such a method includes detecting that dissolved oxygen levels in the wine have increased. The increase in dissolved oxygen levels indicates that the wine has spoiled or is nearing spoilage. The beverage diagnostic device is configured to detect dissolved oxygen levels in the wine contained by the wine bottle. In one implementation, the beverage diagnostic device is configured to detect dissolved oxygen levels in the wine contained by the wine bottle as at least a portion of the wine flows through the beverage diagnostic device. A method of diagnosing freshness or quality of a beverage may also include detecting that free sulfur dioxide has been consumed in the beverage.

A method of diagnosing wine may also include measuring a change in the aroma of the wine. For example, such a method may include programming a sensor to respond to various levels of acetaldehyde odors, coupling the sensor to a wine bottle or other wine container and using the sensor to detect the aroma change of the wine contained in the wine bottle. The sensor may include or may be part of an electronic nose, or may incorporate, in whole or in part, electronic nose technology. Such electronic nose technology may include an odor reactive polymer sensor array and/or a pattern recognition system, such as an artificial neural network (ANN), enabling the sensor to process new odors based on a pattern of aromas created by earlier experiences. Levels of acetaldehyde may be correlated with the level of oxidation of the wine. In one embodiment, the sensor may be part of a beverage diagnostic device that is coupled to the wine bottle and may be used alone or in conjunction with one or more of the other measurement techniques discussed herein.

In other examples, methods of diagnosing wine may include detecting or measuring an increase in acetaldehyde in the wine. For example, such a method may include programming a sensor to detect increases in acetaldehyde levels, coupling the sensor to a wine bottle or other wine container, and using the sensor to detect the increase in acetaldehyde in the wine contained in the wine bottle. The sensor may be part of a beverage diagnostic device that is coupled to the wine bottle. This measurement method may be used alone or in conjunction with one of the other measurement techniques described herein.

A method of diagnosing wine may also include measuring changes in ethanol levels in the wine or in the headspace of the wine bottle. Such methods may include providing a sensor to detect changes in ethanol levels, coupling the sensor to a wine bottle or other wine container, and using the sensor to detect the changes in ethanol levels in the wine contained in the wine bottle. This measurement method may be used alone or in conjunction with one or more of the other measurement techniques described herein.

Figure 22:
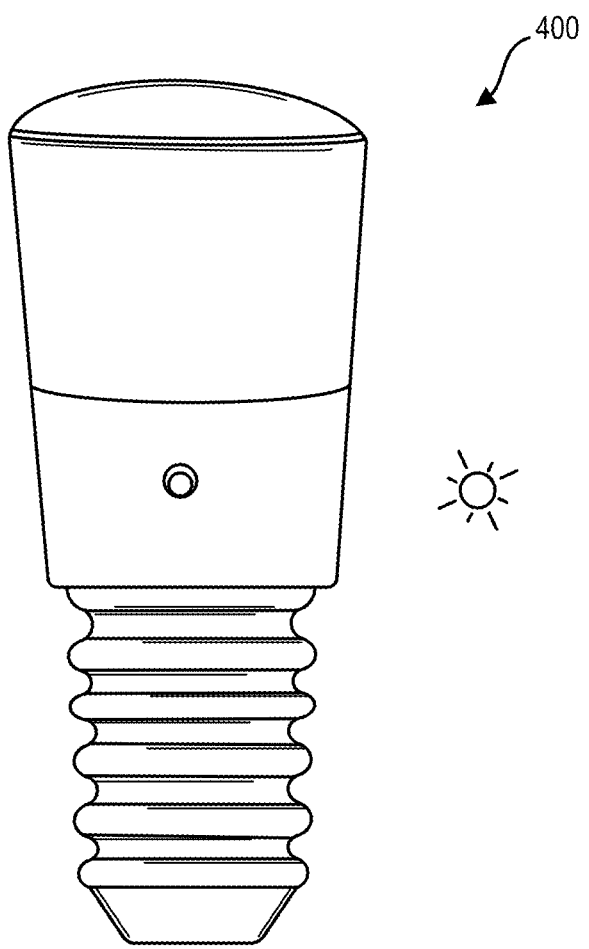
FIG. 22 is an elevational view of a wine bottle stopper, according to an exemplary embodiment.
Figure 23:
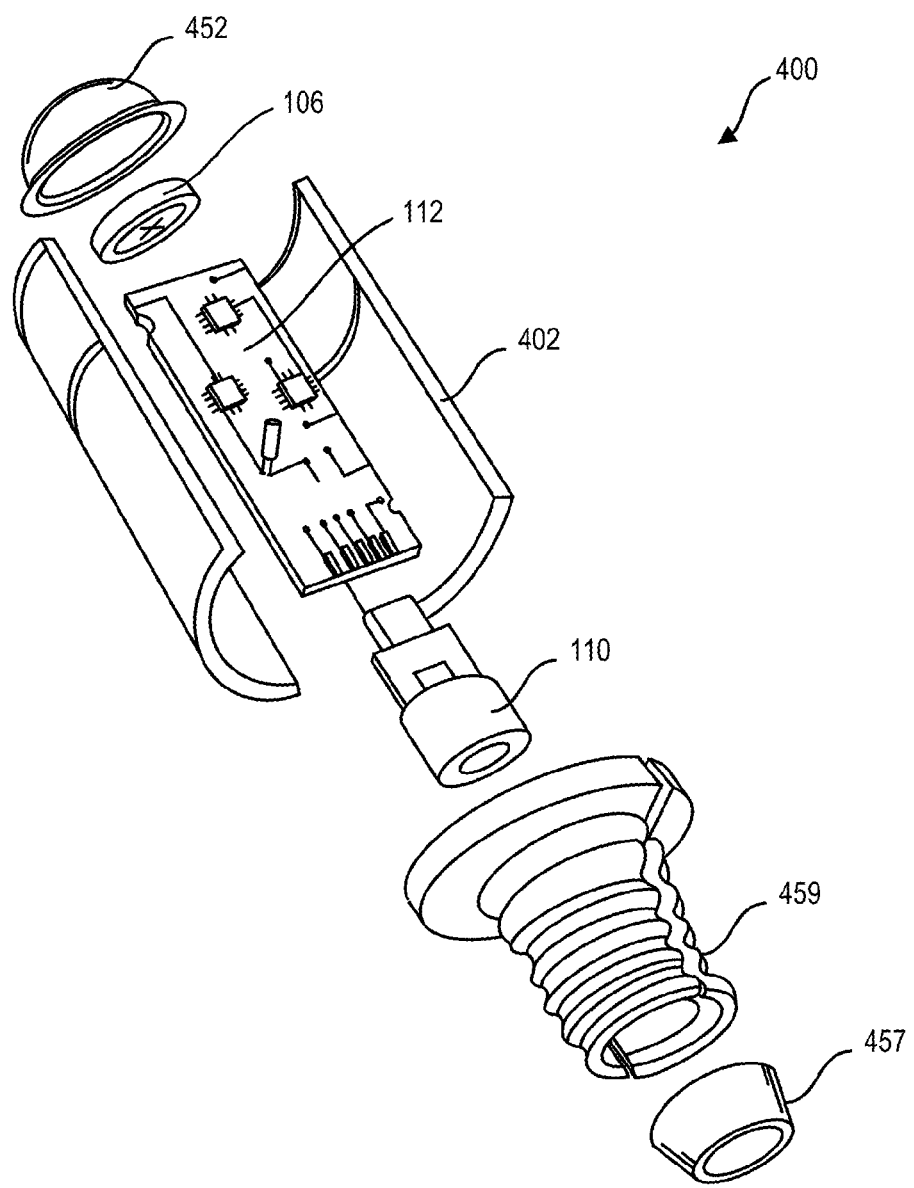
FIG. 23 is an exploded view of the wine bottle stopper of FIG. 22, according to an exemplary embodiment.

FIG. 22 illustrates an elevation view of a wine bottle stopper 400. FIG. 23 illustrates an exploded view of wine bottle stopper 400. Wine bottle stopper 400 includes a housing 402, a switch 452 connected to one end of housing 402, a sealing element 459 connected to the other end of housing 402, and a sensor cover connected to sealing element 459. Sensor 110 is disposed within the sealing element 459 and/or the sensor cover. Battery 106 and circuit board 112 are electrically connected and are at least partially disposed within housing 402. Switch 452 is in electrical communication with circuit board 112. Sensor 110 is in electrical communication with circuit board 112. An LED, other type of light, or other indicator is in electrical communication with circuit board 112 and is positioned proximate housing 402 and/or the sealing element 459. circuit board 112 includes one or more controllers, which are in electrical communication with battery 106, sensor 110, and the LED or other indicator. Wine bottle stopper 400 may include any of the features, functions, elements, or characteristics of any of the other apparatuses, wine bottle stoppers, and/or beverage diagnostic devices disclosed herein In one example, wine bottle stopper 400 may be characterized as a replacement cork. In one implementation, switch 452 includes a push-button switch, a toggle switch, a momentary contact switch, a proximity switch, or any combination thereof. Sealing element 459 may be a ribbed rubber tubular component or other elastomer tubular component adapted to sealingly engage the inside surface of the neck of the wine bottle. Wine bottle stopper 400 may provide a liquid tight and/or air tight seal within the neck of the wine bottle. In one implementation, sensor 110 includes sniffer technology. In some examples, sensor 110 includes, or is, a free sulfur dioxide sensor. Sensor 110 may include, in whole or in part, one or more of the following sensors or portions thereof: Sulfur Dioxide Sensor Part Number 008-1113-000, which is available from RAE Systems, Inc., San Jose, Calif.; Sulfur Dioxide Sensor SKU Number OXA-502, which is available from Variable, Inc., Chattanooga, Ten.; Sulfur Dioxide Sensor Model DM-700-502, which is available from Detcon, Inc., The Woodlands, Tex.; S02-D4 Sulfur Dioxide Sensor, which is available from Alphasense Ltd, Great Notley, United Kingdom, and S02-A4 Sulfur Dioxide Sensor, which is also available from Alphasense Ltd, Great Notley, United Kingdom.

Figure 24:
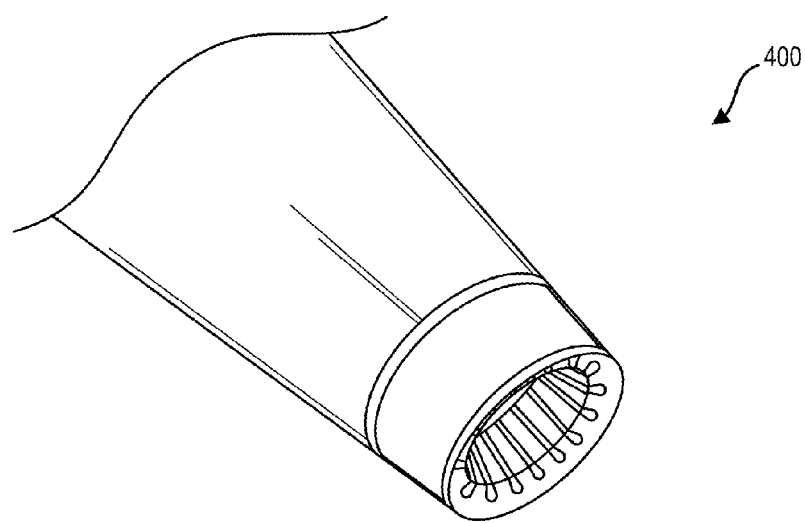
FIG. 24 is a perspective view of a portion of the wine bottle stopper of FIGS. 22 and 23, according to an exemplary embodiment.
Figure 25:
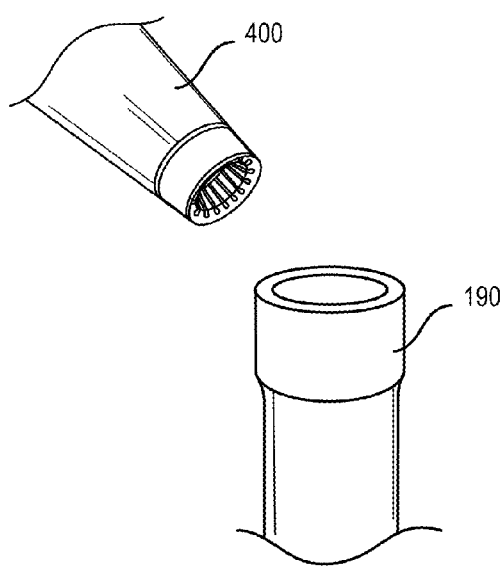
FIG. 25 is a perspective view of the wine bottle stopper of FIGS. 22-24, according to an exemplary embodiment.

FIG. 24 is a perspective view of a portion of wine bottle stopper 400. FIG. 25 includes various perspective views of wine bottle stopper 400 that may be inserted to a neck of wine bottle 190. In operation, with continuing reference to FIGS. 22-25, a cork or cap is initially removed from a wine bottle. When it is desired to close and seal the wine bottle, wine bottle stopper 400 of FIGS. 22-25 is used. More particularly, the sealing element is inserted into the wine bottle to sealingly engage the inside surface of the neck of the wine bottle. Thus, wine bottle stopper 400 replaces the cork.

When it is desired to drink additional wine, the switch is activated, causing the battery to supply electrical power to the sensor via the electrical circuitry or PCB. The sensor or sensors detect whether there is sulfur dioxide in the headspace, that is, the space within the wine bottle that extends between the liquid and the wine bottle stopper. If the sensor or sensors detect sulfur dioxide in the headspace (e.g., the sensor detects a level of sulfur dioxide above a predetermined threshold level or the sensor detects a level of sulfur dioxide above a predetermined threshold for a specified period of time), the sensor(s) transmit one or more signals to the circuitry or PCB, which, in turn, causes the LED or other light to emit light, indicating that the wine is palatable, fresh, or "good." If the sensor(s) do not detect sulfur dioxide in the headspace, or detect a level of sulfur dioxide that is below a predetermined threshold level, the LED or other light does emit light, indicating that the wine is not palatable, not fresh, or "bad." In other examples, a sulfur dioxide level in a range between "good" and "bad," may also be indicated as "marginal, "OK," or "acceptable." As described herein, the sulfur dioxide measurement may be used in conjunction with one or more other measurements.

In some examples, electrical power may be continuously provided to one or more of the electrical components of the device and the switch may be omitted. In another example, the device may not be powered or make measurements continuously but may power up periodically to make measurements and display the condition of the wine.

Figure 26:
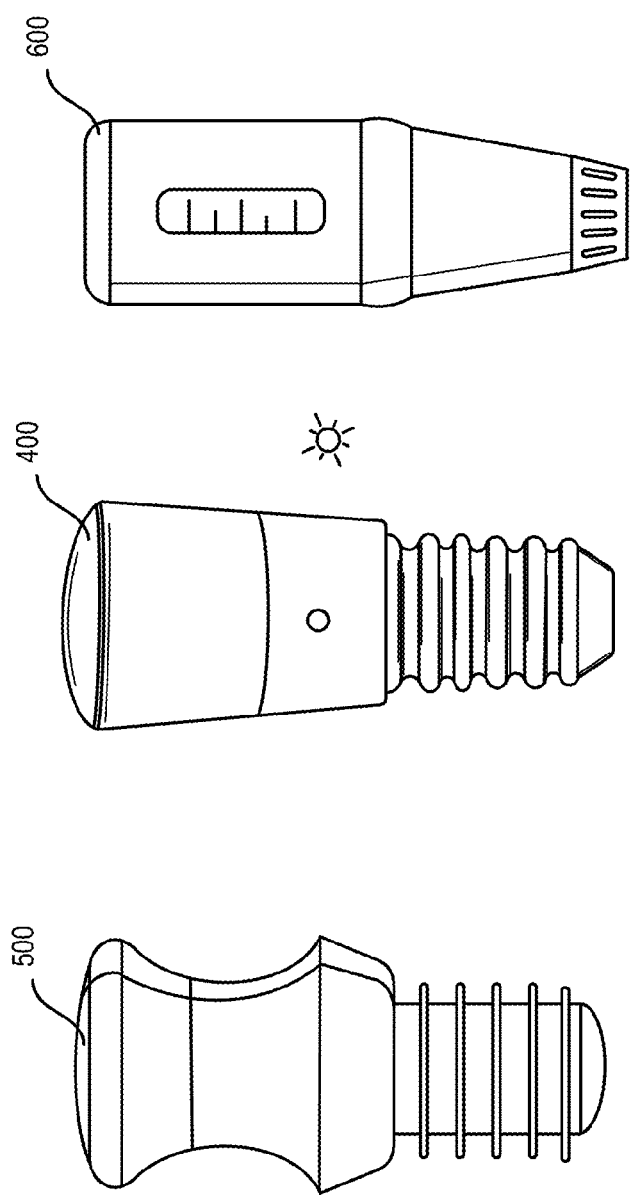
FIG. 26 includes elevational views of wine bottle stoppers according to respective exemplary embodiments.

FIG. 26 illustrates elevational views of wine bottle stoppers 400, 500, and 600. Wine bottles stoppers 500 and 600 may include any of the features, functions, elements, or characteristics of any of the other apparatuses, wine bottle stoppers, and/or beverage diagnostic devices disclosed herein. Wine bottle stopper 600 includes a display scale for indicating the measure wine quality or freshness. The display scale is in electrical communication with the circuitry or PCB and the scale indicates the degree to which the wine is fresh (bad, good, fresh, marginal, etc.). In some cases, the display scale may be implemented using a non-volatile display element, such as with an e-ink display.

Figure 27:
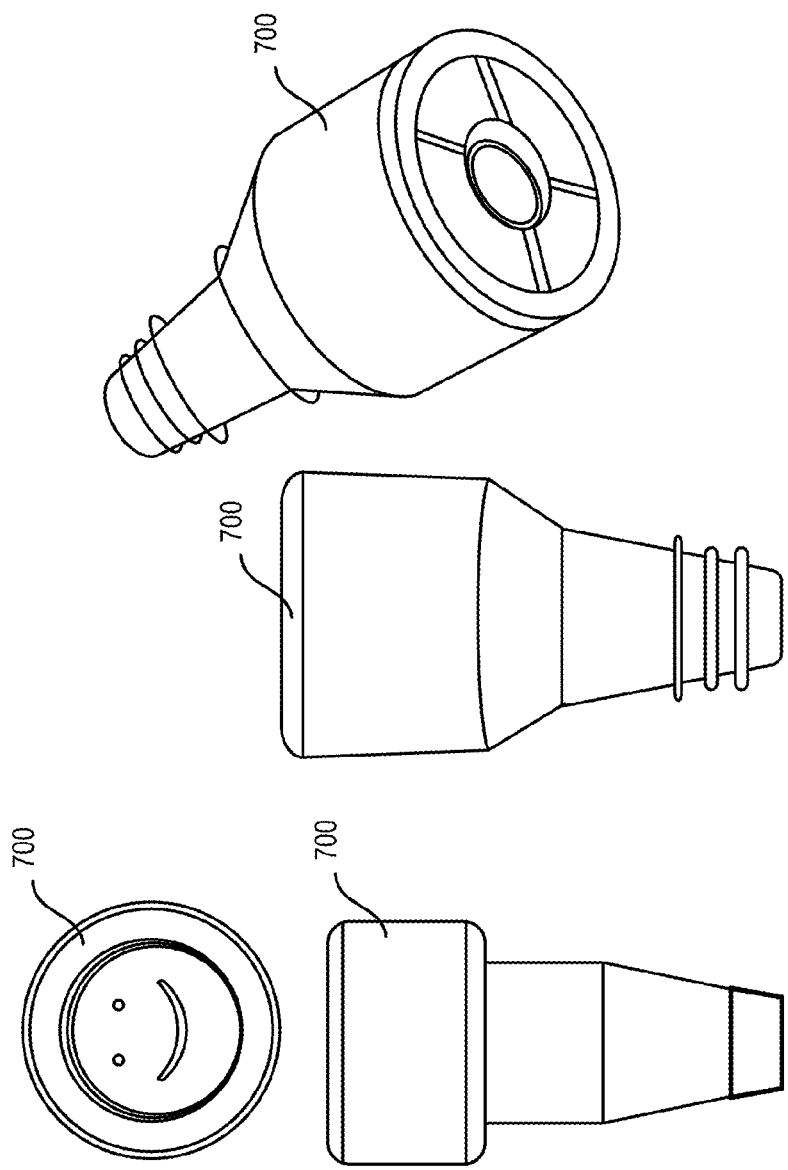
FIG. 27 includes views of wine bottle stoppers according to respective exemplary embodiments.

FIG. 27 illustrates wine bottle stopper 700 that includes a freshness indicator on a top of the stopper. The freshness indicator may include elements that further convey the quality of the wine, such as with a controllable icon or symbol, such as with a smiley face. Any of the disclosed wine bottle stoppers may or may not include a sensor cover. Wine bottle stopper 700 may include any of the features, functions, elements, or characteristics of any of the other apparatuses, wine bottle stoppers, and/or beverage diagnostic devices disclosed herein.

Figure 28:
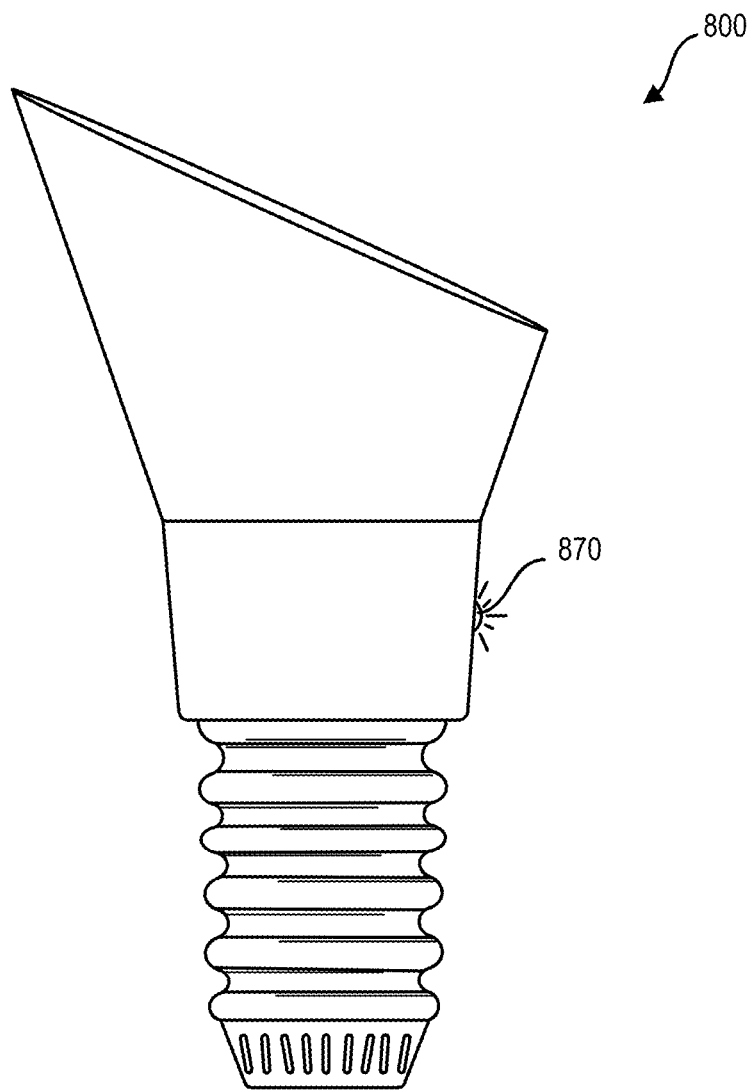
FIG. 28 is an elevational view of a wine bottle stopper according to another exemplary embodiment, the wine bottle stopper including one or more beverage diagnostic device features, aspects, or elements.
Figure 29:
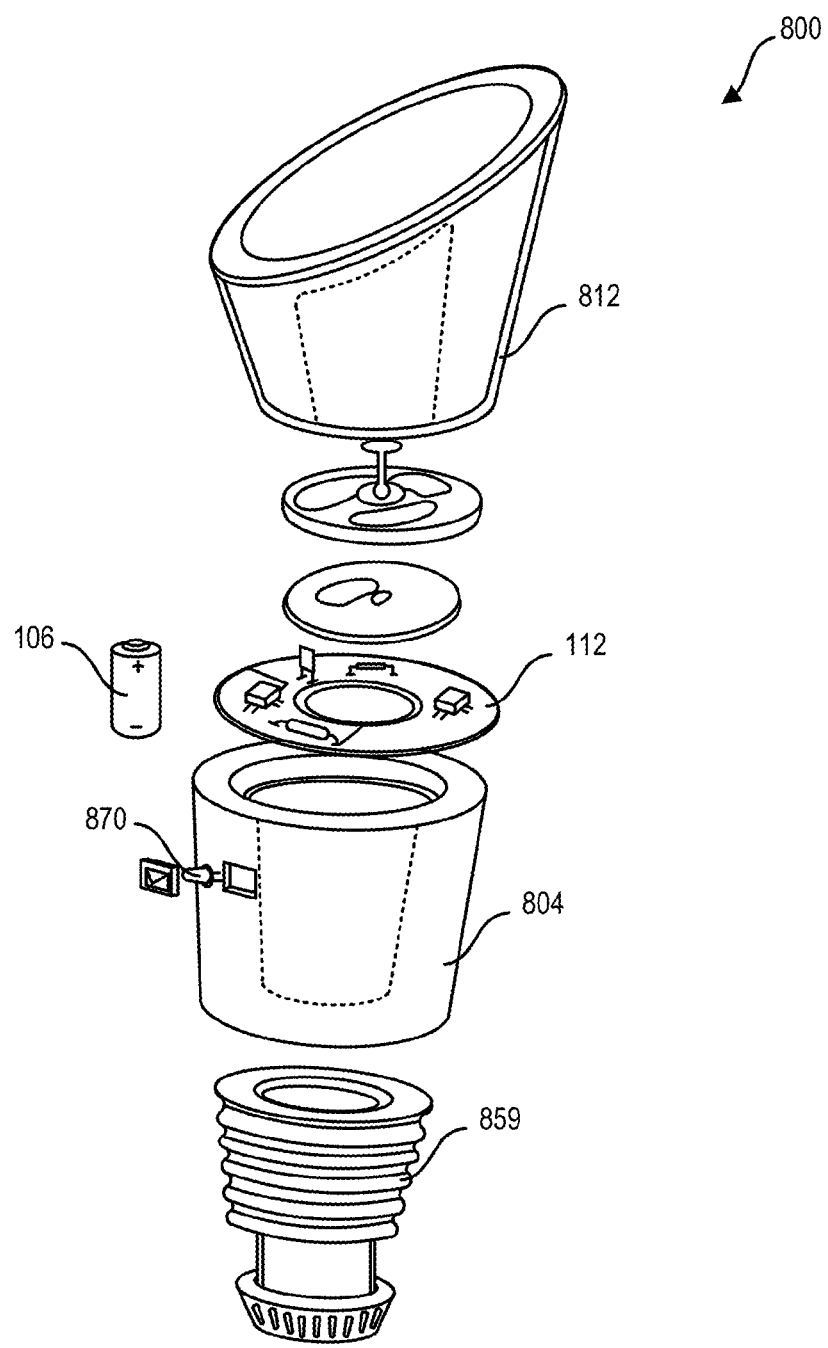
FIG. 29 is an exploded view of the wine bottle stopper of FIG. 28, according to an exemplary embodiment.

FIG. 28 illustrates a side view of a wine bottle stopper 800 that also includes a wine spout for pouring the wine. Wine bottle stopper 800 may include any of the features, functions, elements, or characteristics of any of the other apparatuses, wine bottle stoppers, and/or beverage diagnostic devices disclosed herein. As illustrated in FIG. 29, wine bottle stopper 800 may include a pour spout 812, a housing connected to the spout 804, a sealing element 859 connected to housing 804 and opposing spout 812, a sensor connected to sealing element 859 and opposing housing 804, and an LED 870, other type of light source, or other indicator positioned within or proximate an opening formed in housing 804.

Figure 30:
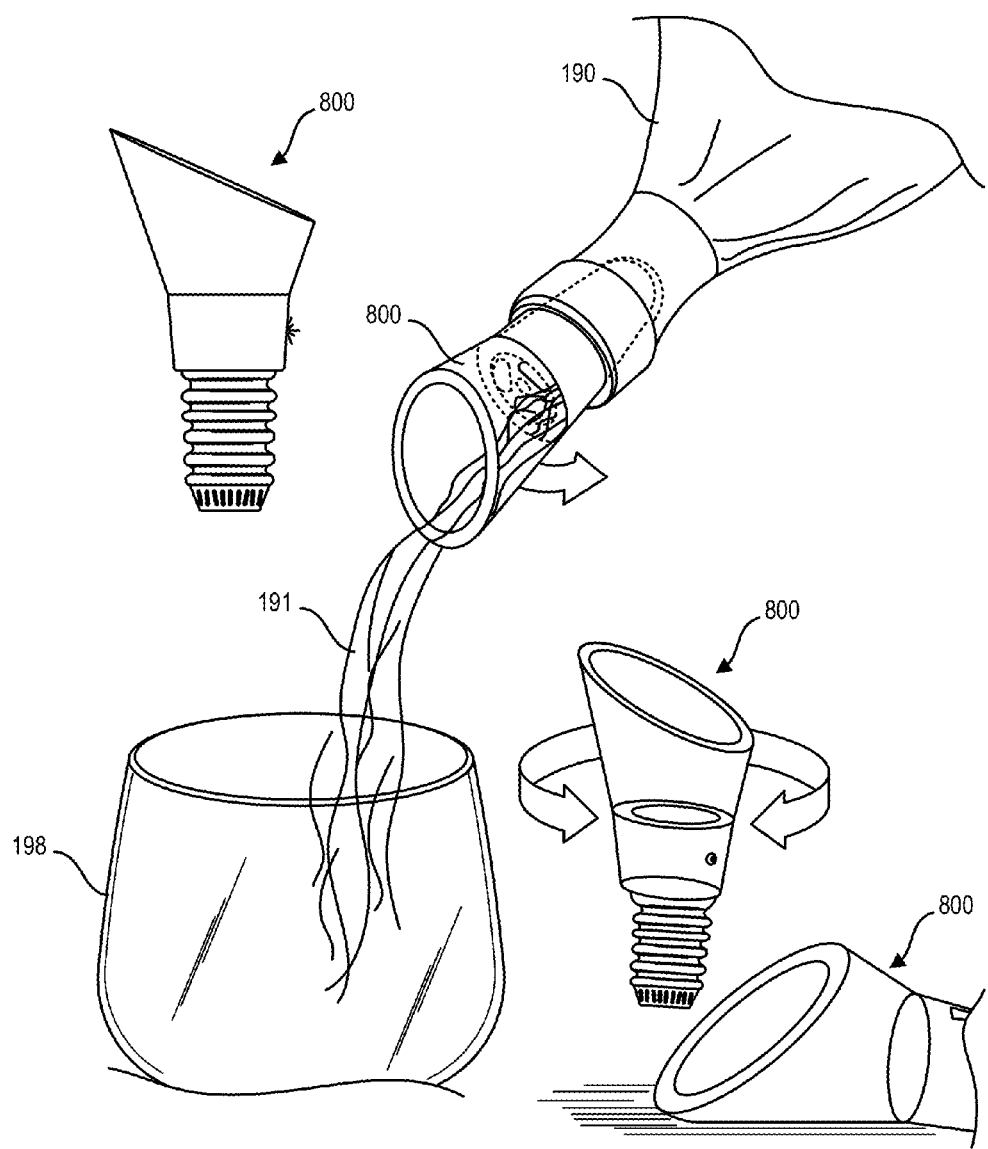
FIG. 30 includes views of the wine bottle stopper of FIGS. 28 and 29, according to respective exemplary embodiments.

Wine bottle stopper 800 may further include an opener, a blocker, an annular shaped circuit board 112, a battery 106, and a lens. The opener may include a disc component with an opening formed therethrough. The blocker may include a disc component and a plurality of openings formed therethrough. One of the opener and the blocker may be connected to the lower end portion of the pour spout, and the other of the opener and the blocker may be connected to the upper end portion of the housing. Relative rotation between the pour spout and the housing is permitted; thus, relative rotation between the opener and the blocker is permitted. The bottle stopper 800 can be rotated to a closed position, as shown in FIG. 30, to provide an airtight seal, thereby allowing the container 190 to be placed in a non-upright position without risk of leakage of wine from the container. Each of the battery, the LED or other light, and the sensor is in electrical communication with the circuitry or PCB. The lens is connected to the housing and covers the LED or other light. At least the circuitry, the lens, and the battery may be disposed within the housing.

FIG. 30 illustrates use of wine stopper 800. A cork or cap is removed from wine bottle 190 when the wine bottle is initially opened. When it is desired to close wine bottle 190, wine bottle stopper 800 is used. More particularly, the sealing element is inserted into wine bottle 190 and sealingly engages the inside surface of the neck of the wine bottle. Thus, wine bottle stopper 800 replaces the cork. The battery supplies electrical power to the sensor(s) via the circuitry or PCB. The sensor(s) detect whether there is sulfur dioxide in the headspace, that is, the space within wine bottle 190 that extends between the liquid and the wine bottle stopper. If the sensor(s) detect sulfur dioxide in the headspace, the sensor(s) transmit one or more signals to the circuitry, which, in turn, causes the LED or other light to emit light, indicating that the wine is palatable, fresh, or "good." If the sensor does not detect sulfur dioxide in the headspace, the LED or other light does emit light, indicating that the wine is not palatable, not fresh, or "bad."

When it is desired to drink additional wine, the LED or other light is observed to see if it emits light to determine whether the wine is still fresh. If drinking the wine is still desired, relative rotation is effected between the pour spout and the housing so that the opening in the opener is at least partially aligned with one of the openings in the blocker. After the respective openings are so aligned, wine is poured out of wine bottle 190 into glass 198. In some examples, the poured wine flows through the sensor, the sealing element, the housing, the aligned openings, and the pour spout. In some examples, to close wine bottle 190, relative rotation between the pour spout and the housing of the wine bottle stopper is effected so that no openings are aligned.

In some examples, the beverage diagnostic devices or wine bottle stoppers disclosed herein may include an aeration device and/or features configured to promote aeration of the wine. In some cases, the aeration device may be included in or combined with one or more other components of the beverage diagnostic devices or wine bottle stoppers disclosed herein, such as with filter 144.

Figure 31:
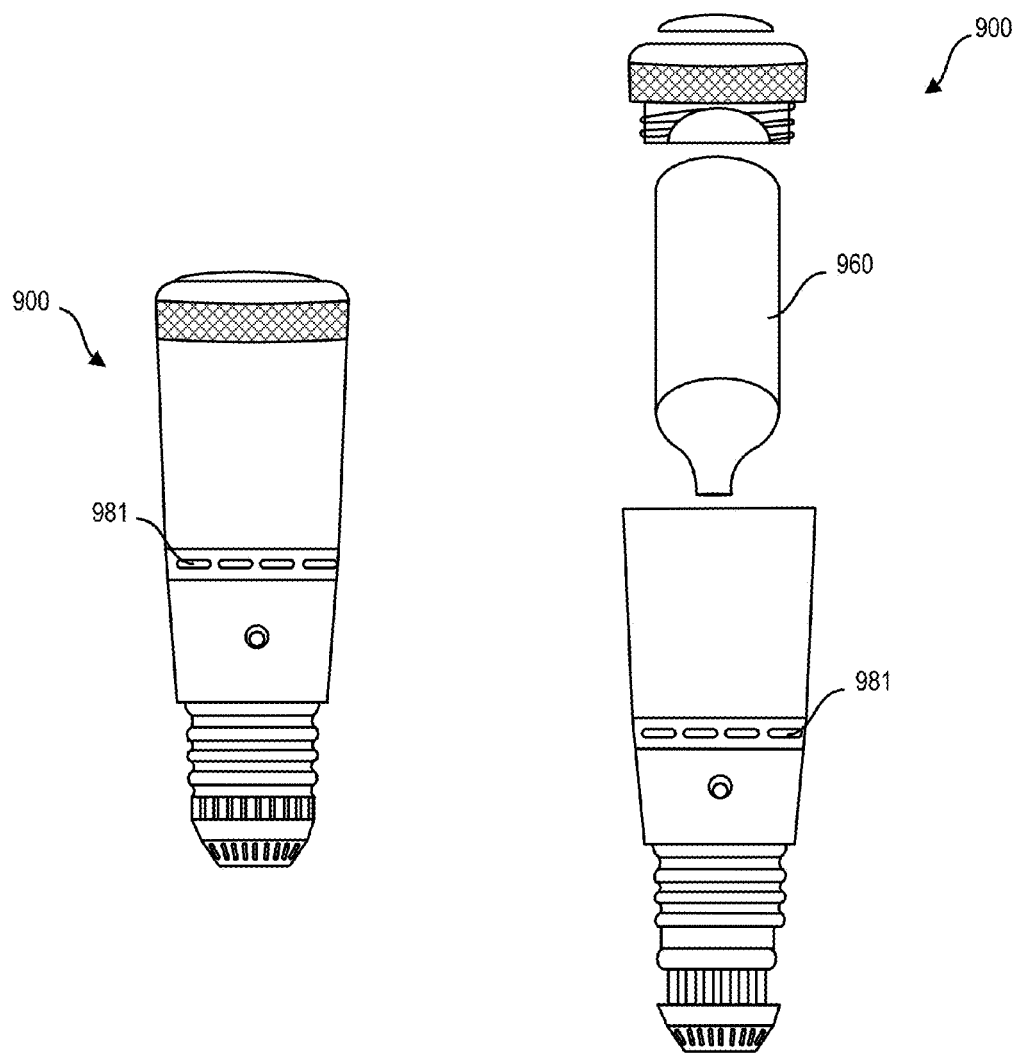
FIG. 31 includes elevational and partially exploded views of a wine bottle stopper according to yet another exemplary embodiment, the wine bottle stopper including one or more wine preservation features, aspects, or elements.

FIG. 31 includes an elevational view and a partially exploded view of a wine bottle stopper 900. Wine bottle stopper 900 includes a plurality of circumferentially-spaced openings 981 that are formed at the upper end portion of the housing. A tubular member is connected to the upper end portion of the housing. A pressure vessel 960, which may be a pressurized argon cartridge, is disposed within the internal region of the tubular member. The internal region of the tubular member is adapted to be in fluid communication with the internal region of the wine bottle. A top cap is connected to the upper end portion of the tubular member. A button is connected to the top cap and is operably coupled to the argon cartridge. Wine bottle stopper 900 may include any of the features, functions, elements, or characteristics of the other wine bottle stoppers and beverage diagnostic devices disclosed herein.

Figure 32:
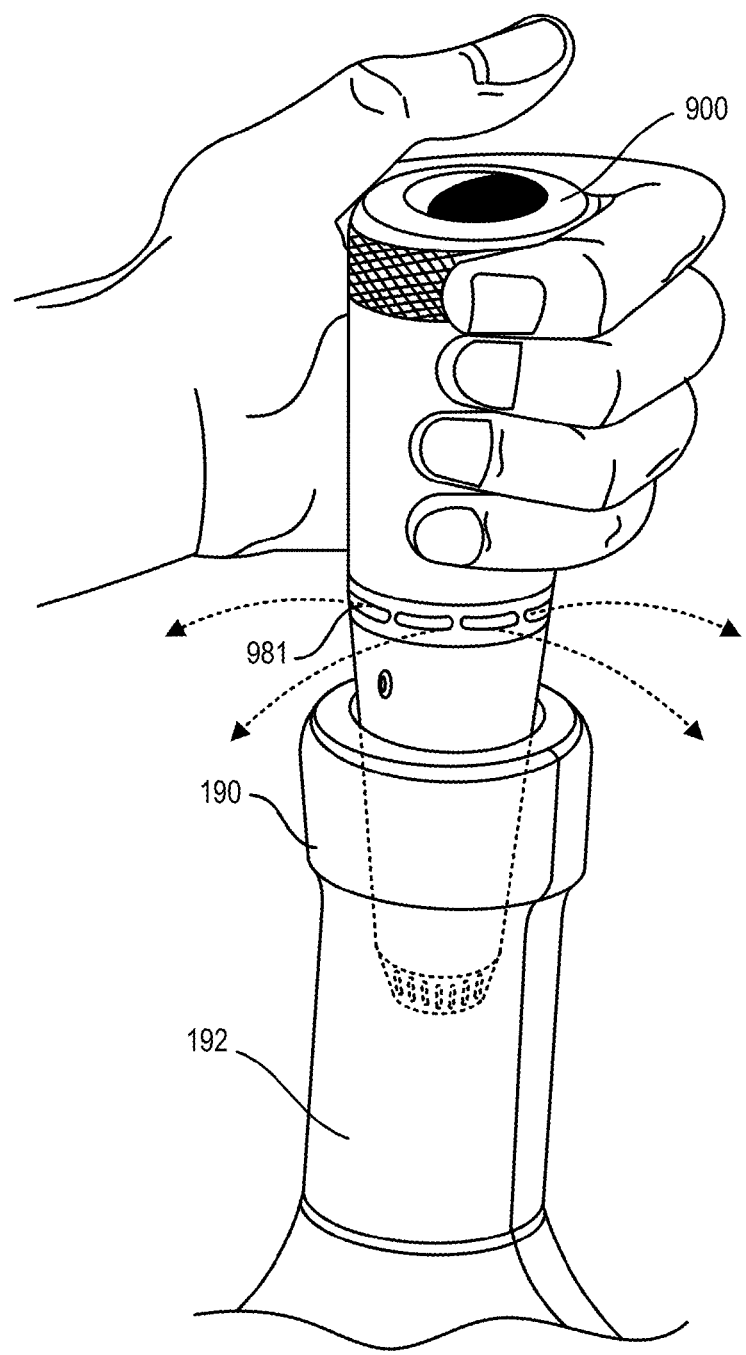
FIG. 32 includes a perspective view of the wine bottle stopper of FIG. 31.

FIG. 32 illustrates operation of wine bottle stopper 900. In operation, wine bottle stopper 900 operates in a manner similar to the other wine bottle stoppers and beverage diagnostic devices disclosed herein. Additionally, to preserve the freshness of the wine, argon, is introduced into wine bottle 190 when wine bottle stopper 900 is coupled to wine bottle 190. More particularly, the button is depressed, causing the argon cartridge to release argon into the headspace of the wine bottle and forcing oxygen to flow out of circumferentially-spaced openings 981. As a result, oxygen is purged from the headspace of the wine bottle, thereby preserving the freshness of the wine. In an exemplary embodiment, circumferentially-spaced openings 981 may include a one-way valve (each individually or a single valve associated with all of the openings) that is operably coupled thereto. The one-way valve(s) permits the oxygen to flow out of the headspace via the corresponding opening, but do not permit any gases to flow into the headspace via the openings. Wine bottle stopper 900 may include any of the features, functions, elements, or characteristics of any of the other apparatuses, wine bottle stoppers, and/or beverage diagnostic devices disclosed herein.

In several exemplary embodiments, instead of an argon cartridge, wine bottle stopper 900 may include a cartridge charged with another type of gas, such as another type of inert gas (e.g., nitrogen, helium).

Figure 33:
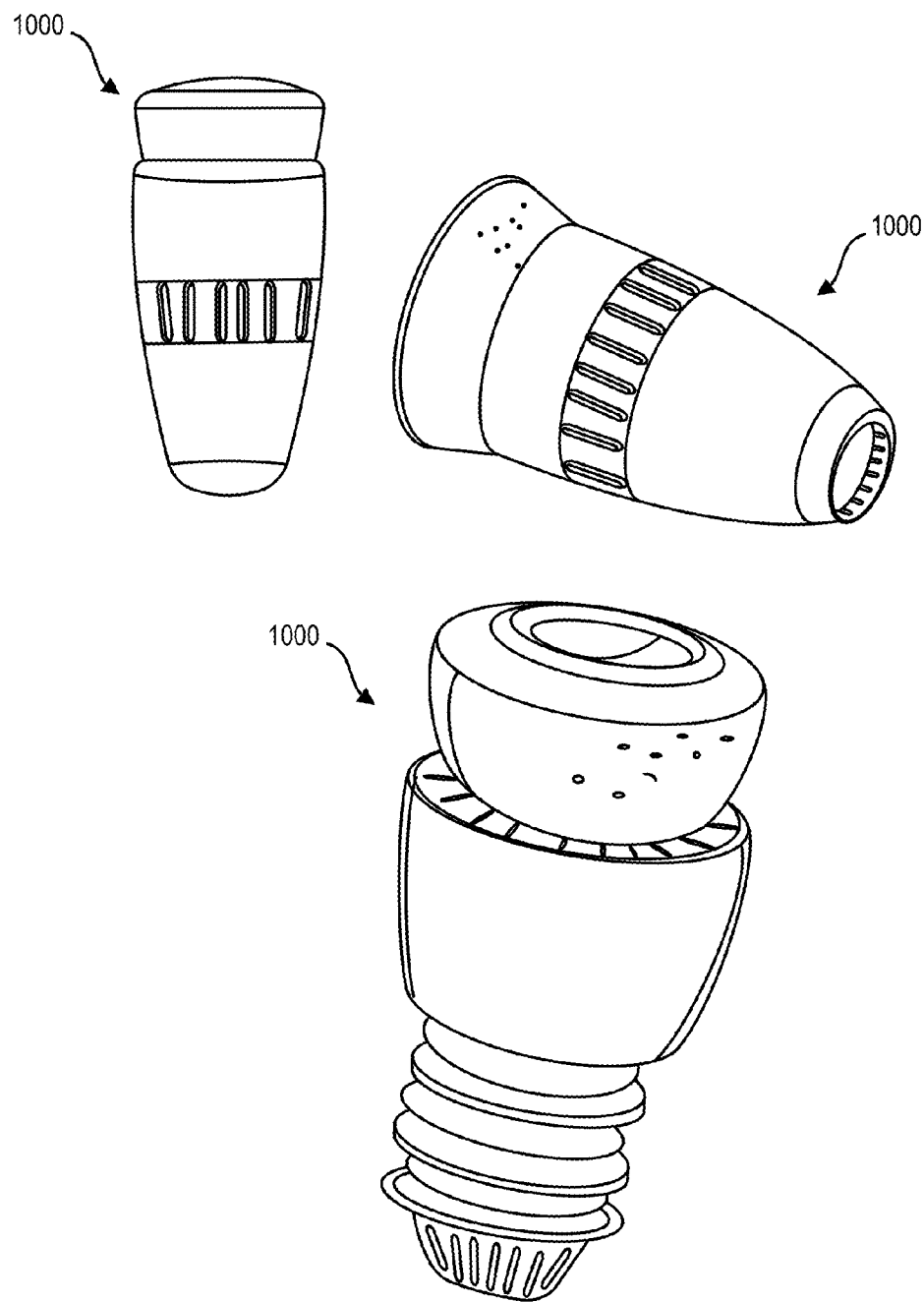
FIG. 33 includes views of wine bottle stoppers according to still yet other exemplary embodiments, each of the wine bottle stoppers including one or more wine preservation features, aspects, or elements.
Figure 34:
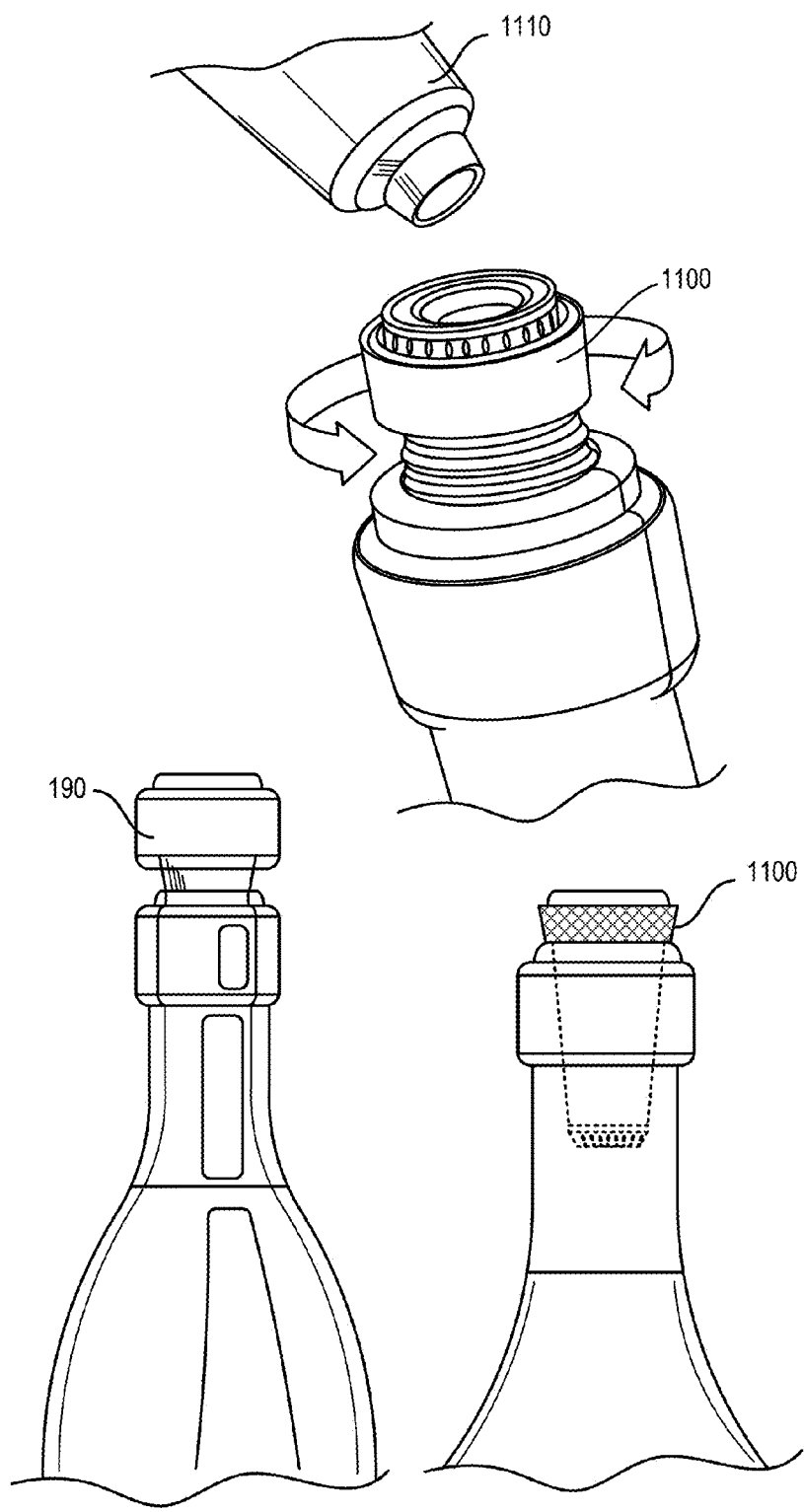
FIG. 34 includes views of a system according to an exemplary embodiment, the system including a wine bottle stopper and a preservation device.

FIG. 33 illustrates various views of a wine bottle stopper 1000. Wine bottle stopper 1000 may include a sensor, a housing connected to the sensor and including sealing features, a plurality of circumferentially-spaced openings formed in the housing, and a pressurized cartridge extending into the housing, the cartridge including a button. The other of the illustrated wine bottle stoppers includes a sensor, a sealing element connected to the sensor, a housing connected to the sealing element and defining an axially-facing surface, a plurality of circumferentially-spaced openings formed in the axially-facing surface, and a pressurized cartridge extending into the housing, the cartridge including a button. In several exemplary embodiments, the operation of wine bottle stopper 1000 may be similar to the operation of any of the other beverage diagnostic devices and/or wine bottle stoppers disclosed herein. Wine bottle stopper 1000 may include any of the features, functions, elements, or characteristics of any of the other apparatuses, wine bottle stoppers, and/or beverage diagnostic devices disclosed herein FIG. 34 illustrates a system including a wine bottle stopper 1100 and a wine preservation device 1110. Wine bottle stopper 1100 may include any of the features, functions, elements, or characteristics of any of the other apparatuses, wine bottle stoppers, and/or beverage diagnostic devices disclosed herein. Wine bottle stopper 1100 further includes a one-way valve at the top thereof. A plurality of circumferentially-spaced openings is formed at the upper end portion of the housing. The housing is rotatable, relative to at least the sealing element and the sensor.

Preservation device 1110 is a portable, handheld device. Preservation device 1110 includes a housing and an adapter at one end thereof. An argon cartridge is disposed in the housing and is adapted to release pressurized argon via the adapter. In several exemplary embodiments, instead of argon, the housing includes a cartridge charged with another type of gas, such as another type of inert gas (e.g., nitrogen, helium). In several exemplary embodiments, the cartridge is omitted and the charged gas is disposed in the housing, contacting the inside surface of the housing. In one specific embodiment, preservation device 1110 also includes a switch connected to the housing.

To pour wine out of an attached wine bottle, the housing of wine bottle stopper 1110 is twisted relative to at least the sealing element, causing a through-passage to form in the wine bottle stopper and allowing the wine to be poured out through wine bottle stopper 1110. After the wine has been poured, to close the wine bottle, the housing is again twisted relative to at least the sealing element, removing the through-passage.

Figure 35:
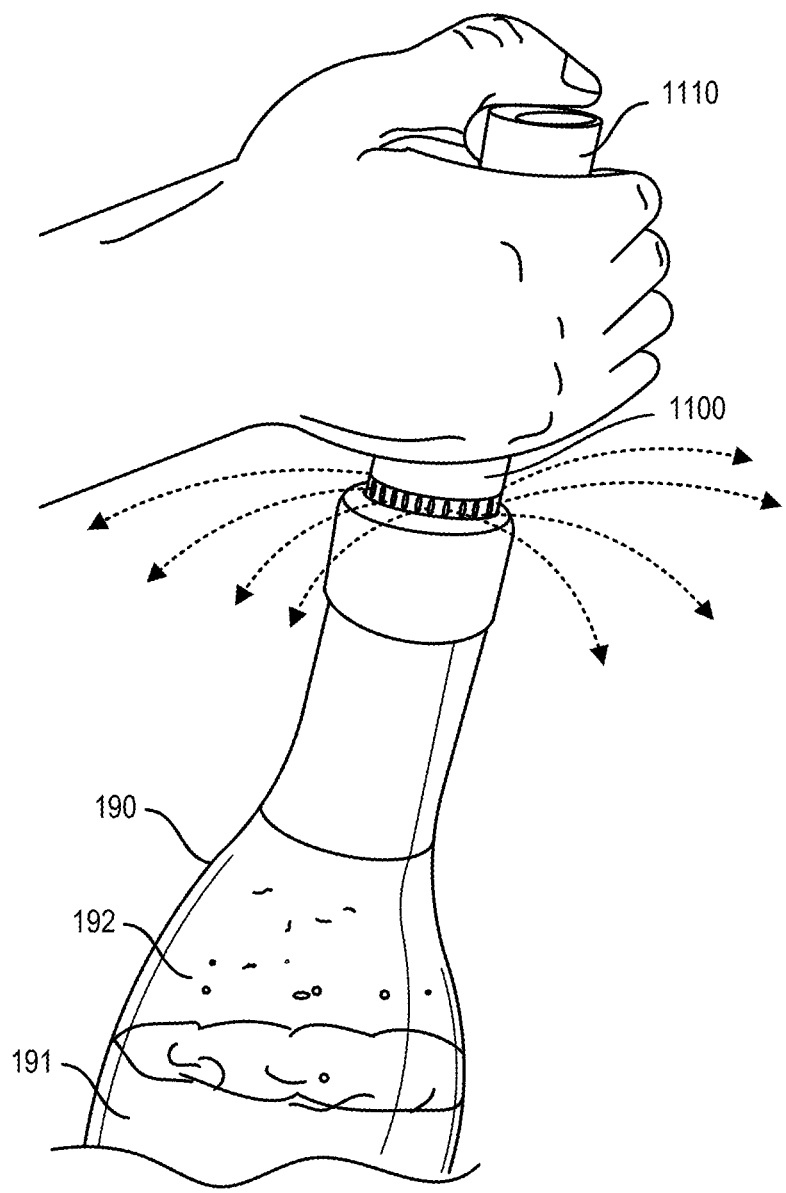
FIG. 35 is a perspective view of the system of FIG. 34, according to an exemplary embodiment.
Figure 36:
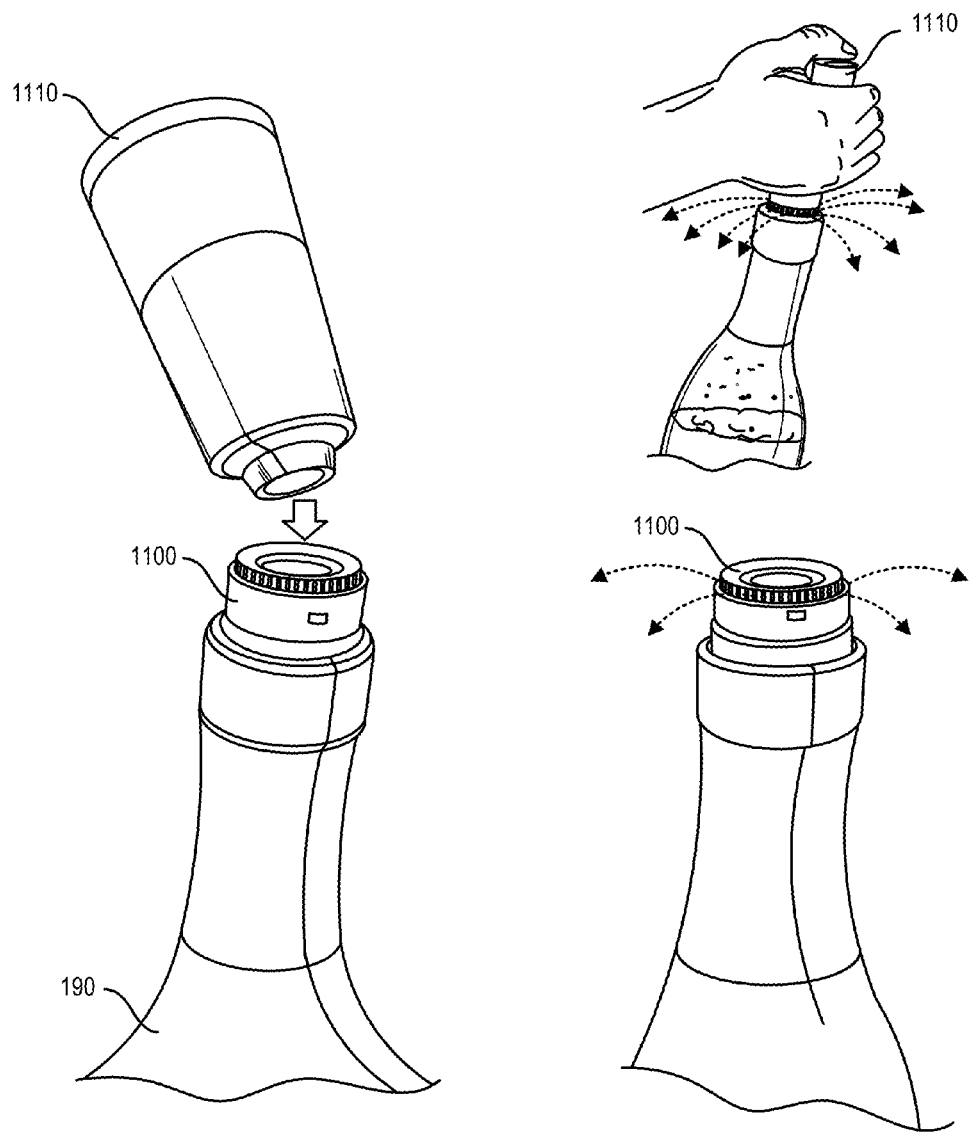
FIG. 36 is a perspective view of a system according to an exemplary embodiment, the system including the system of FIGS. 34 and 35, as well as additional wine bottle stoppers.

Additionally, to preserve the freshness of the wine, preservation device 1110 is temporarily coupled to wine bottle stopper 1100 when wine bottle stopper 1100 is installed on the wine bottle 190, as illustrated in FIGS. 35 and 36. The adapter of preservation device 1110 extends into and/or engages the one-way valve of the housing of wine bottle stopper 1100. The switch on the housing of preservation device 1110 is activated, causing the argon cartridge to release pressurized argon, which flows through the adapter and the one-way valve and into the headspace of the wine bottle. As a result, oxygen in the headspace is forced to flow out of the headspace via the circumferentially-spaced openings formed in the housing of wine bottle stopper 1100. As a result, oxygen is purged from the headspace of the wine bottle, thereby preserving the freshness of the wine. Preservation device 1110 is then decoupled from the wine bottle stopper by pulling the adapter out of, and/or disengaging the adapter from, the one-way valve of wine bottle stopper 1100. The one-way valve at the top of the housing of wine bottle stopper 1100 permits the argon to flow into the headspace, but does not permit backflow of any fluid or oxygen.

FIG. 37 illustrates test results for an experiment involving measuring sulfur dioxide and hydrogen sulfide ($H_2S$) in two bottles of wine. The data was collected using a gas chromatograph detector with chemiluminescence detector. The first four line items in the table show concentrations of sulfur dioxide and hydrogen sulfide in an unopened bottle of red wine and an unopened bottle of white wine. To allow data to be collected without opening the bottles of wine, samples were collected by inserting a syringe through each bottle's cork. As is shown in the table, prior to opening the bottles, the liquid concentration of sulfur dioxide was about 26 ppm (parts per million) for both bottles of wine, whereas the gas concentration of sulfur dioxide in the headspace was only about 6-9 ppm. Once the bottle of red wine was opened, the concentration of sulfur dioxide in the headspace dropped off sharply while the concentration of sulfur dioxide in the liquid gradually declined. In one example, a method for determining wine quality can include measuring a concentration of sulfur dioxide in liquid wine or in the headspace and determining the freshness of the wine based on the measured concentration of sulfur dioxide. The wine may be deemed fresh (i.e. good) if the concentration of sulfur dioxide in the liquid is greater than about 5, 10, 15, 20, or 25 ppm. The wine may be deemed not fresh (i.e. bad) if the concentration of sulfur dioxide in the liquid is less than about 5, 10, 15, 20, or 25 ppm. In one example, the wine may be deemed not fresh if the sulfur dioxide level is below less than about 1.0 ppm, the wine may be deemed marginally fresh if the sulfur dioxide level is about 1.0-1.5 ppm, and the wine may be deemed fresh if the sulfur dioxide level is greater than about 1.5 ppm. The sulfur dioxide concentrations determined by the sulfur dioxide sensor can depend on the sensitivity of the sensor. In one example, where the sensitivity of the sulfur dioxide sensor is 180 nA/ppm, the wine may be deemed not fresh if the sulfur dioxide level is below less than about 1.18 ppm, the wine may be deemed marginally fresh if the sulfur dioxide level is about 1.18-1.75 ppm, and the wine may be deemed fresh if the sulfur dioxide level is greater than about 1.75 ppm. In another example, where the sensitivity of the sulfur dioxide sensor is 360 nA/ppm, the wine may be deemed not fresh if the sulfur dioxide level is below less than about 0.59 ppm, the wine may be deemed marginally fresh if the sulfur dioxide level is about 0.59-0.87 ppm, and the wine may be deemed fresh if the sulfur dioxide level is greater than about 0.87 ppm. When the wine is deemed fresh, an indicator light 870 may appear green. When the wine is deemed marginally fresh, the indicator light may appear yellow. When the wine is deemed not fresh, the indicator light may appear red. When a less sensitive and lower cost sulfur dioxide sensor is used, the marginally fresh indication may be omitted.

Experimental testing revealed that absorbance of the wines decreased with time after they were opened. A method for determining wine freshness can include measuring absorbance of wine in a container, and determining freshness of the wine based on the absorbance. In one example, a method can include measuring the absorbance of wine at about 400-600, 450-550, 500-550, 428, or 520 nm (nanometers), and determining freshness of the wine based on the absorbance. In another example, a device for determining wine freshness can include a sensor capable of measuring absorbance at about 400-600, 450-550, 500-550, 428, or 520 nm. In other examples, a device for determining wine freshness can include a sensor capable of measuring absorbance at about 700-800, 800-900, or 940 nm.

Figure 38:
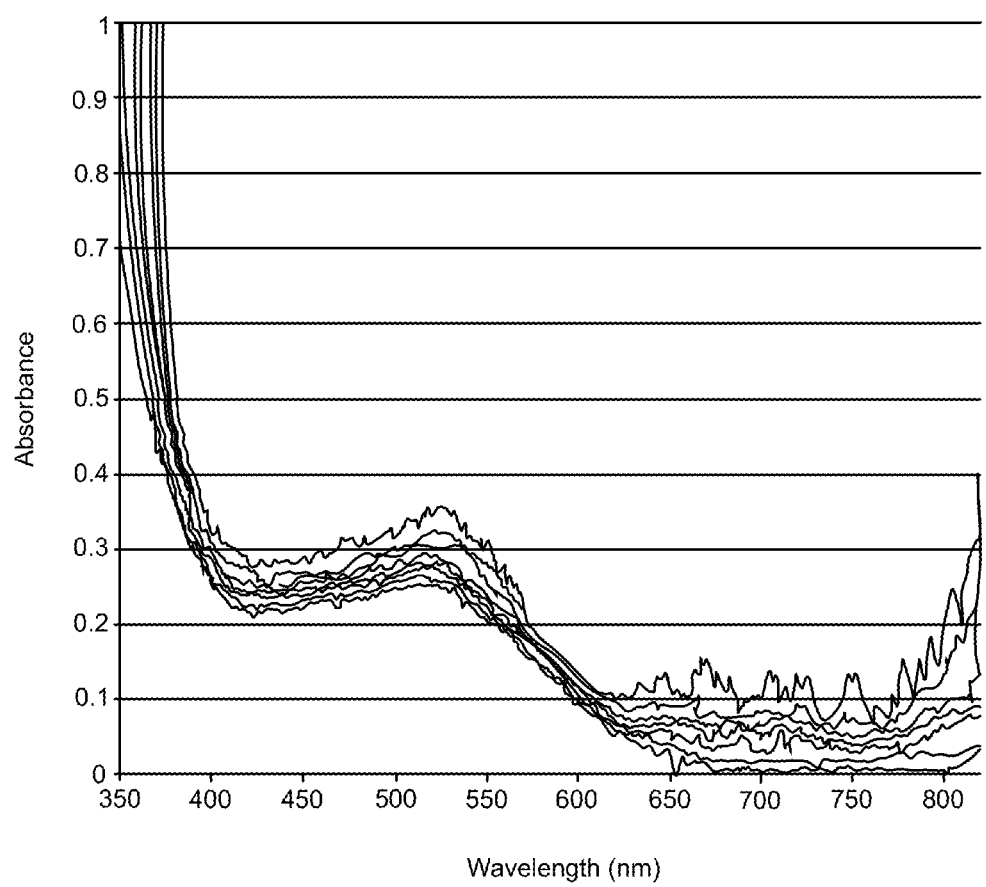
FIG. 38 illustrates spectral data for the experiment introduced in FIG. 37. The x-axis shows wavelength in nanometers, and the y-axis shows absorbance.

FIG. 38 illustrates a graph of spectral data results for the experiment discussed above with respect to FIG. 37. The x-axis of the graph is the optical wavelength of the emitted optical energy in nanometers. The y-axis of the graph is absorbance of the emitted optical energy.

Figure 39:
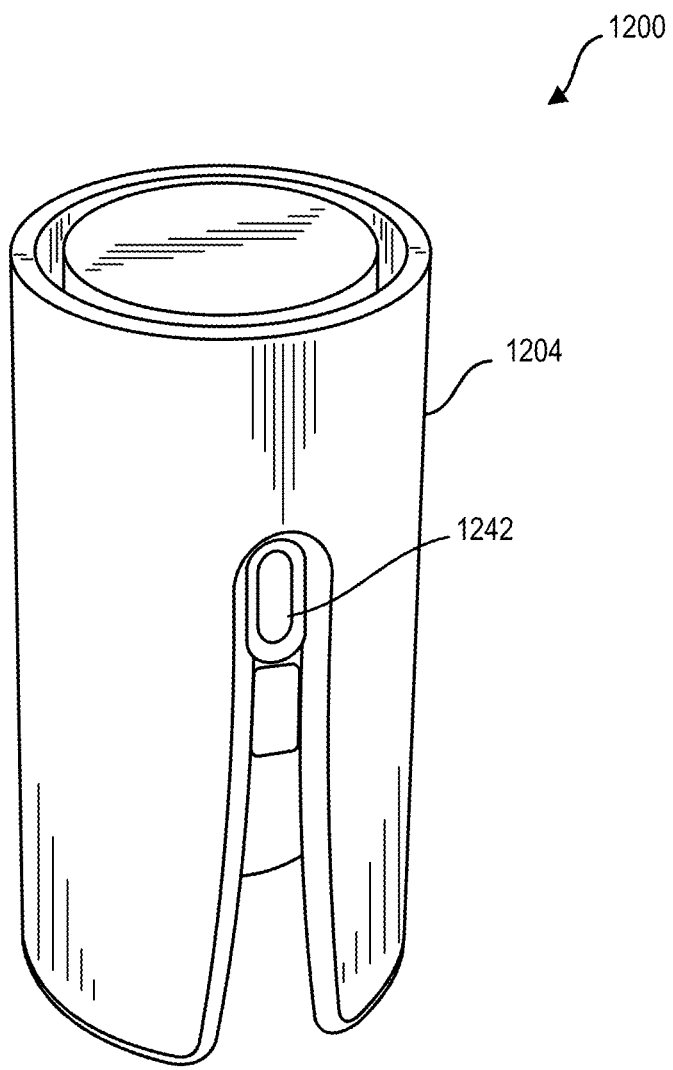
FIG. 39 illustrates an apparatus for determining freshness or wine stored in a container.

FIG. 39 illustrates an apparatus 1200 for determining freshness of wine stored in a container. Apparatus 1200 includes components housed in housing 1204 and indicates freshness of the wine on an indicator 1242.

Figure 40:
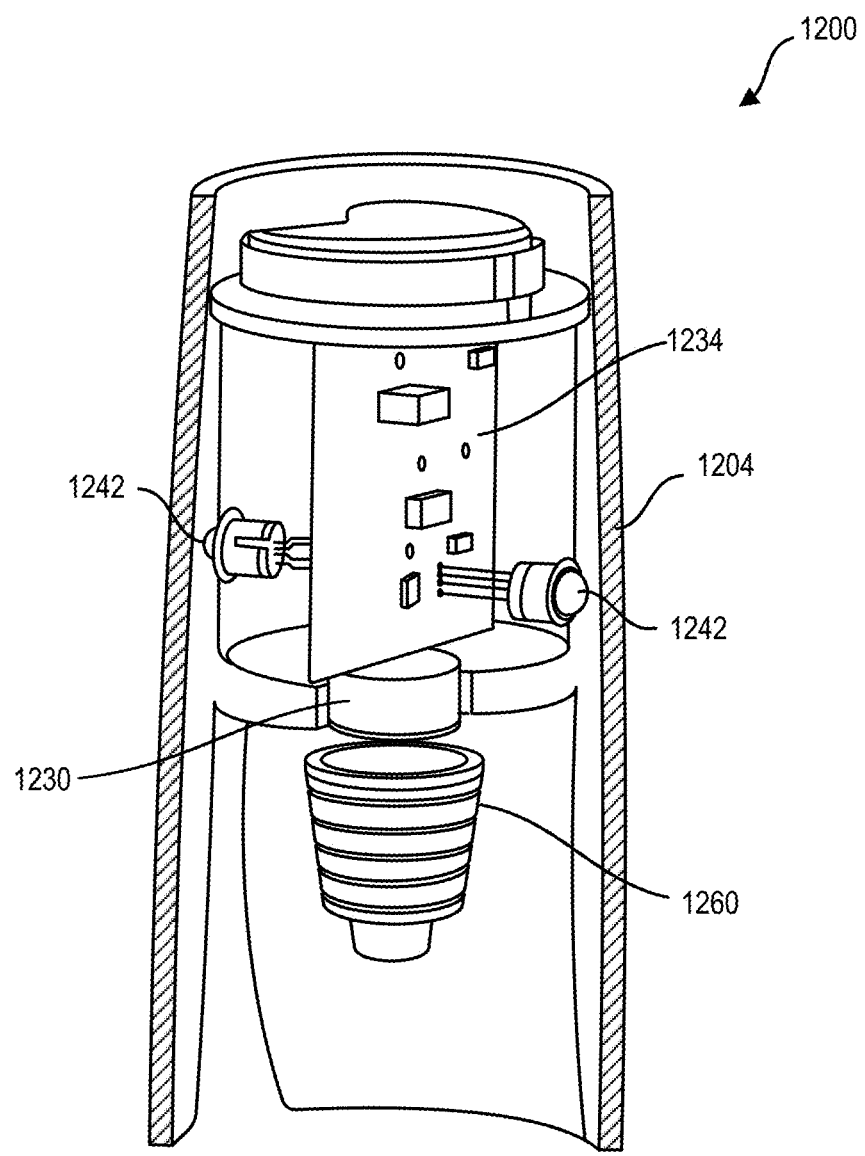
FIG. 40 illustrates a cross sectional view of the apparatus of FIG. 39.

FIG. 40 illustrates a cross sectional view of apparatus 1200. Housing 1204 is removably attachable to a wine bottle such that it spans the opening of the wine bottle and seals to the neck of the bottle with a seal 1260. Apparatus 1200 includes a gas sensor 1230 that is affixed to apparatus 1200 such that it extends into the headspace of the bottle above the wine when housing 1204 is attached to the bottle. Apparatus 1200 may also include an optical sensor pair (not visible) for making optical measurements that further provide insight into gas levels in the headspace. The optical sensor pair includes an optical emitter and an optical detector. The optical sensor pair may also be a PEDD. The optical sensor pair may be positioned such that it extends into the headspace above the wine when housing 1204 is attached to the bottle. The optical emitter and optical detector are positioned such that optical energy emitted from the optical emitter is transmitted through at least a portion of the headspace of the wine bottle toward the optical detector such that the amount of optical energy received at the optical detector varies based in proportion to amounts of one or more gases in the headspace.

Apparatus 1200 also contains electrical circuitry 1234 that is contained in housing 1204 and is electrically interfaced to gas sensor 1230 and to the optical sensor pair. In some examples, gas sensor 1230 may include a sulfur dioxide sensor. Electrical circuitry 1234 operates the gas sensor to generate a series of gas level measurements each indicating a measured level of a gas in the headspace. The series of gas level measurements may indicate gas level measurements made over a period of time. Electrical circuitry 1234 also operates the optical sensor pair to generate a series of optical transmission measurements each indicating a level of optical transmission of the emitted optical energy through the portion of the headspace. The series of optical transmission measurements may indicate optical level measurements made over a period of time. A quality parameter corresponding to the freshness of the wine is determined based on both the series of gas level measurements and the series of optical transmission measurements in order produce a more accurate, reliable, and/or stable quality measure.

Electrical circuitry 1234 may display the resulting quality parameter on one or more of the display elements 1242. In one example, each of display elements 1242 includes a multicolor LED display element wherein different colors are displayed to indicate various quality parameter values. Other types of display elements or devices are possible.

In some configurations, apparatus 1200 may include a filter positioned in proximity to gas sensor 1230. The filter may be positioned for shielding gas sensor 1230 from vapor, such as water vapor or ethanol vapor from the wine. The filter may minimize, reduce, or eliminate undesirable effects vapor may have on gas sensor 1230 and/or measurements made using gas sensor 1230. This filter may be a different filter than filter 144 of FIG. 11. In one specific example, the filter may include a 0.45 μm filter paper.

In some configurations, apparatus 1200 may include a liquid resistant membrane for preventing wine from reaching gas sensor 1230, the optical sensor pair, electrical circuitry 1234, and/or from reaching any other component of apparatus 1200. The membrane may be used as an alternative to or in combination with the vapor filter discussed above.

It is typically desirable to keep a bottle of wine sealed from outside air to the extent possible to reduce the wine's rate of degradation. However, gas sensor 1230 may operate more reliably if it has a fresh source of air. Therefore, apparatus 1200 may include a port (not illustrated) permitting air from outside the container and/or from outside apparatus 1200 to reach gas sensor 1230 for improving operation of gas sensor 1230. In some cases, gas sensor 1230 may contain an aqueous solution of sulfuric acid or propylene carbonate, polytetrafluoroethylene, polycarbonate, noryl polymer, carbon, and one or more precious metals.

Because it is enclosed, the gases in the headspace of a bottle of wine may not be equally distributed throughout the headspace. Consequently, the headspace measurements described herein may provide variable results depending on where in the headspace the measurement is made and may also vary over time depending on factors such as temperature and whether or not the bottle has been moved recently. Therefore, the performance of apparatus 1200 may be improved by including a gas circulation device that circulates the gases in the headspace to provide a more even distribution of those gases throughout the headspace. In one example, the gas circulation device may be a fan operated by a battery and or electrical circuitry of the apparatus. In another example, the gas circulation may be powered by a solar element included in the device or apparatus. In yet another example, the gas circulation device may include a manual hand pump operated by a user of the apparatus. The user may temporarily operate the hand pump before a quality reading is made.

Figure 41:
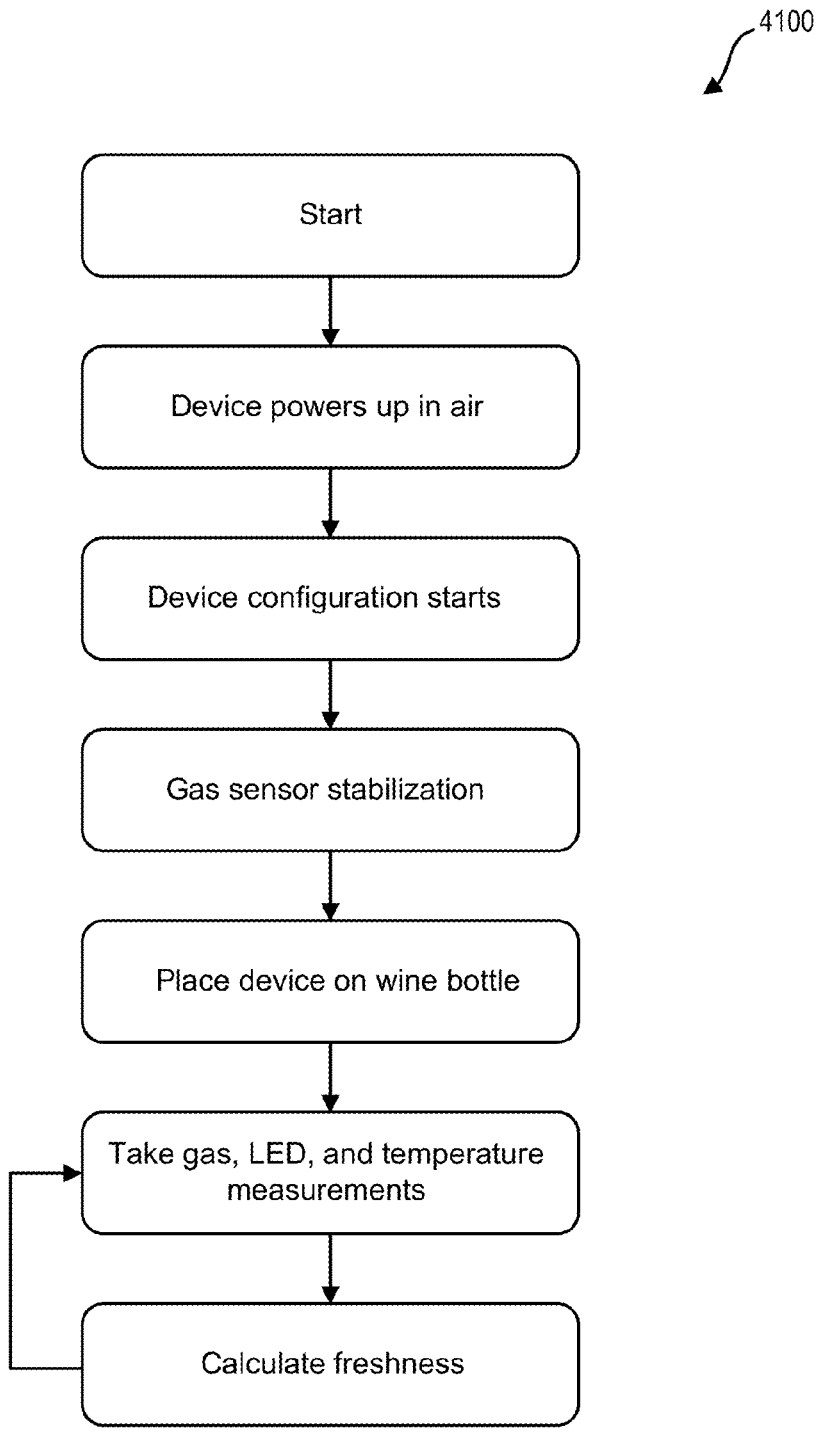
FIG. 41 illustrates a method of operating a device for monitoring freshness of an opened bottle of wine.

The optical emitter of apparatus 1200 may include one or more LEDs. LEDs may be selected based on their primary optical output wavelength. As described above, different wavelengths may be preferable for detecting different types of gases. Different wavelengths may also be preferable depending on the type of wine being measured. In one example, the optical emitter may include an LED that has a primary output wavelength of approximately 428 nm. In another example, the optical emitter may include an LED that has a primary output wavelength of approximately 940 nm. Other output wavelengths are possible. The optical detector may be paired with the optical emitter in the sense that the optical emitter may be designed or configured to detect primarily optical energy in a wavelength range the same or similar to that of the emitter. The optical emitter and/or detector may be band-limited to a particular wavelength or range of wavelengths. Apparatus 1200 may include any of the features, functions, elements, or characteristics of any of the other apparatuses, wine bottle stoppers, and/or beverage diagnostic devices disclosed herein FIG. 41 illustrates method 4100 of operating a device for monitoring freshness of an opened bottle of wine. First, the device is powered up in air before it is installed in the bottle of wine. The electrical circuitry in the device configures the device and the gas sensor is allowed to stabilize in air for a settling period. In some cases, the electrical circuitry may monitor the stabilization of the gas sensor and provide a visual or audible indication to the user when the gas sensor has stabilized. The device is then placed on the wine bottle. Then, a series of measurements are periodically made in the headspace of the wine bottle. The measurements may include gas measurements, optical or LED measurements, temperature measurements, and/or other measurements that may relate to the quality, condition, or freshness of the wine. Then, the freshness of the wine is determined or calculated based on one or more of these measurements.

In another example, a device for monitoring freshness of an opened bottle of wine includes a housing, a printed circuit board, a sulfur dioxide sensor, an optical emitter, an optical detector, and a display element. The housing removably attaches to the neck of the bottle. The device includes a measurement portion that extends into the neck of the bottle when the device is attached to the bottle. The printed circuit board includes electrical circuitry. The electrical circuitry may include a computer processor, memory, analog electrical components, digital electrical components, electrical connectors, and/or other electrical components.

The device may also include a sulfur dioxide sensor affixed to the measurement portion of the housing. The sulfur dioxide sensor is positioned in the headspace of the bottle to perform sulfur dioxide level measurements of the headspace when the device is attached to the bottle. The device includes an optical emitter electrically connected to the printed circuit board and positioned to transmit optical energy through at least a portion of the headspace when the device is attached to the bottle. An optical detector is also electrically connected to the printed circuit board and positioned to receive at least a portion of the optical energy transmitted from the optical emitter through the headspace. The optical detector generates electrical signals corresponding to a magnitude of the portion of the optical energy received at the optical detector. The magnitudes, relative magnitudes, polarities, and/or variations of the electrical signals generated by the optical detector provide an indication of the amount of one or more gases in the headspace of the bottle.

While some of the examples provided herein include making optical measurements through the wine, the present example involves making optical measurements of gases in the headspace without the optical path of the measurement extending through the wine or through any fluid. An optical measurement in the headspace may provide some or all of the benefits of making an optical measurement through the wine or fluid, but may also provide one or more other benefits including: not needing to tip or move the wine bottle to make the measurement, not potentially contaminating the wine by introducing foreign objects, avoiding fluid contact between components of the device and the wine, and avoiding any potential cleaning processes when switching a device among bottles of wine.

The electrical circuitry of the device may be adapted or configured to periodically calculate a freshness value for the wine. The freshness value is based on a current sulfur dioxide level measurement received from the sulfur dioxide sensor and a current electrical output of the optical detector. The electrical circuitry is further adapted or configured to update information displayed on the display element based on the calculated freshness value to indicate a freshness of the wine to a user of the device.

A quality parameter or freshness value may be calculated based on current measurements, as well as on past measurements. For example, the freshness value may be calculated based on current measurements and one or more of: a past sulfur dioxide level measurement received from the sulfur dioxide sensor, a past electrical output of the optical detector, and/or a past calculated freshness value or quality parameter.

In one variation, the device may also include wireless communication circuitry for wirelessly communicating with another electrical device and/or for wirelessly transmitting the calculated quality parameter to another device, such as to a centralized display system associated with many bottles of wine or to a computing device over a network. In a further variation, information regarding the quality parameters of various wines at an establishment may be transmitted to or made available on a software application running on a portable electronic device of a patron of the establishment. This configuration can be used, for example, by restaurant personnel to wirelessly monitor the status of all opened bottles of wine and can be used in conjunction with inventory control systems. Collected data can be used to alert personnel that certain bottles of wine are no longer fresh and should be disposed of. Collected data can be used to alert personnel that certain bottles of wine are marginally fresh and should be offered at a discounted price. Collected data can be used to identify brands and vintages of wine that remain fresh for longer periods of time after being opened and can be used to recommend those wines over similar wines that spoil more quickly. The collected data can be viewed using a software application operating on an electronic device, such as a smartphone. A database can include collected data from more than one user and can be accessed by multiple users. In some examples, the collected data in the database can be used by the device to predict, based on collected data from similar wines, when the bottle of wine will no longer be fresh. In this way, the device can not only provide the current status of the wine, but can also provide a predicted date and time of expiration of the wine, which can be used by bars and restaurants to trigger promotional discounts and inventory ordering.

A method of predicting freshness of an opened bottle of wine based on collected data stored in a database can include identifying a type of wine in the opened bottle, searching the database for collected data of the same or similar types of wine (e.g. maker, vintage, etc.), calculating an average lifespan of the same or similar wines based on the collected data, predicting a date and time when the opened bottle of wine will no longer be fresh. The prediction can take into account other factors such as how often the bottle will likely be reopened, initial sulfur dioxide measurements recorded by the device, and current sulfur dioxide measurements by the device. The predicted date and time can be displayed on a display screen of the device. The electrical circuitry in the device can periodically update and revise the prediction based on changes in one or more factors.

In some configurations, the device may include a battery for powering one or more of the electrical circuitry, the sulfur dioxide sensor, the optical emitter, the optical detector, the display element, and/or any other electrical components of the device. In one variation, the battery may be replaceable. In another variation, the battery may be replaceable and the device may include a charging port for attaching a charging cable from an external power source to charge the rechargeable battery. In yet another variation, the device may include a solar panel for generating power for operating the device and/or for charging the battery.

The electrical circuitry may also be configured to enter a sleep mode between measurements and may come out of the sleep mode to periodically make measurements and update the indicator. The device may be configured to come out of the sleep mode to perform these steps once every minute, every 5 minutes, every 10 minutes, every 15 minutes, every hour, every 2 hours, every 4 hours, every 8 hours, every 12 hours, once per day, or on a different time interval.

Figure 42:
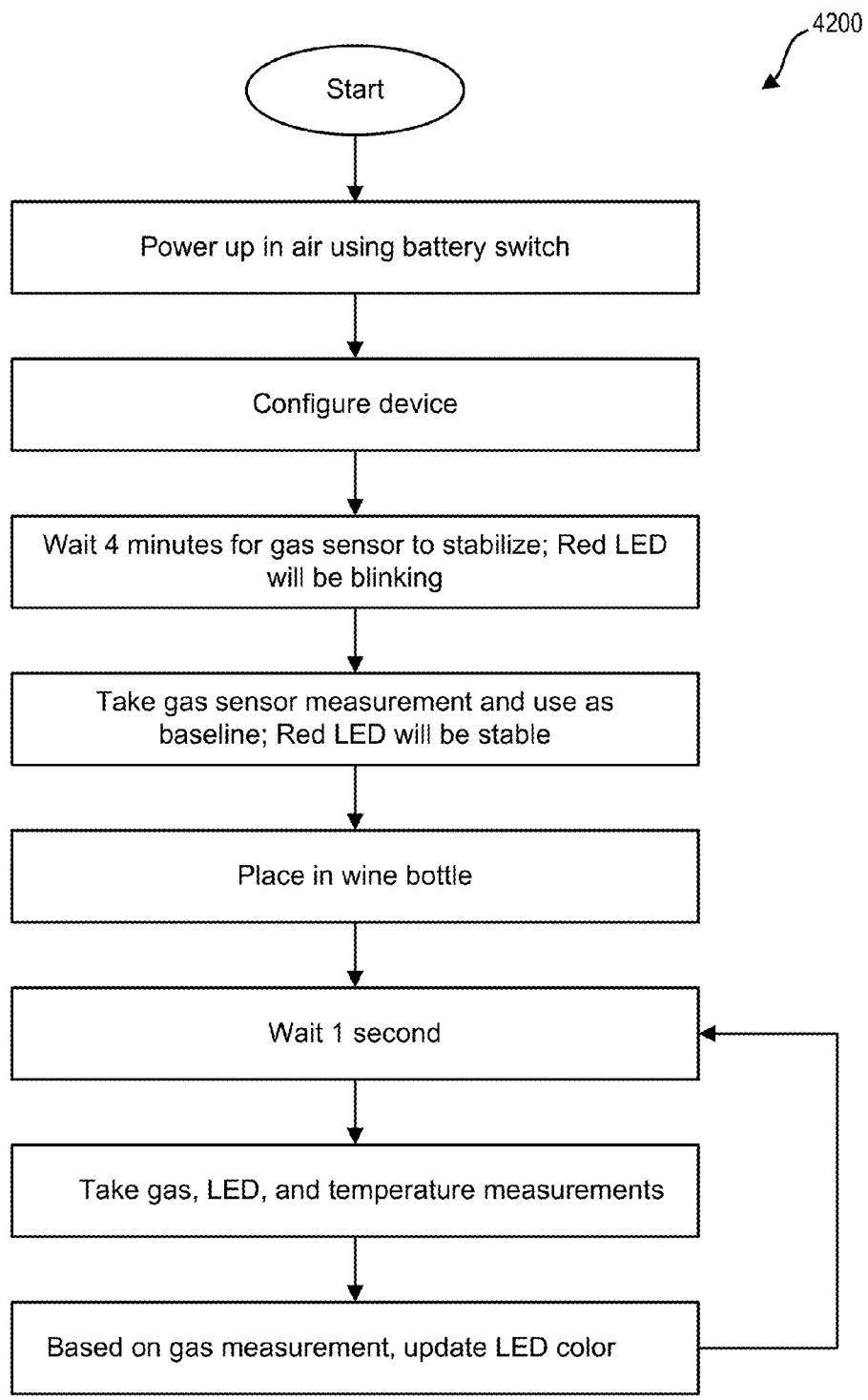
FIG. 42 illustrates another method of operating a device for monitoring freshness of an opened bottle of wine.

FIG. 42 illustrates method 4200 of operating a device for monitoring freshness of an opened bottle of wine. The method includes activating a switch that enables the battery to power up the device. It may be preferable to power up the device in air to stabilize the sensors. In one example, it may be necessary to wait 4 minutes for the gas sensor to stabilize. Other stabilization periods are possible. The device may use a visual indicator to indicate that the sensor(s) are still stabilizing and/or when the stabilization is complete. A baseline measurement may be taken in air before the device is inserted into the bottle. The device is then placed in the wine bottle. Once in the bottle, the device periodically takes measurements and updates an indicator color based on the measurements. While an update period of one second is indicated in FIG. 42, many other periods are possible.

In some examples, in addition to detecting if the wine is good or bad, the devices described herein may also detect if the wine is suitable for use as an ingredient in some other entrée or beverage, such as Sangria. In one example, the device may indicate that the wine is suitable for use as an ingredient about 4, 8, 12, or 24 hours before the wine is deemed bad.

An apparatus can determine freshness of wine stored in a container. The container can have an opening and a headspace above the wine inside the container. The apparatus can include a housing removably attachable to the container such that the housing spans the opening of the container and seals the opening of the container when the housing is attached to the container. The apparatus can include a gas sensor affixed to the housing such that the gas sensor extends into the headspace of the container above the wine when the housing is attached to the container. The apparatus can include an optical sensor pair having an optical emitter and an optical detector. The optical sensor pair can be positioned such that the optical sensor pair extends into the headspace above the wine when the housing is attached to the container. The optical emitter and optical detector can be positioned such that optical energy emitted from the optical emitter is transmitted through at least a portion of the headspace toward the optical detector. The optical emitter can include a light emitting diode (LED). In some examples, the LED can have an output wavelength of approximately 428 nm. In some examples, the LED can have an output wavelength of approximately 940 nm. The apparatus can include electrical circuitry contained in the housing and electrically interfaced to the gas sensor and to the optical sensor pair. The electrical circuitry can be configured to operate the gas sensor to generate a series of gas level measurements each indicating a measured level of a gas in the headspace. The electrical circuitry can be configured to operate the optical sensor pair to generate a series of optical transmission measurements each indicating a level of optical transmission of the emitted optical energy through the portion of the headspace; The electrical circuitry can be configured to determine a quality parameter for the wine, where the quality parameter corresponds to the freshness of the wine and is determined based on both the series of gas level measurements and the series of optical transmission measurements. The apparatus can include a visual display element, and the electrical circuitry can be configured to display the quality parameter for the wine on the visual display element. The gas can include sulfur dioxide, and the gas sensor can be a sulfur dioxide sensor. A decreasing amount of the sulfur dioxide in the headspace as indicated by the series of gas level measurements can indicate a decrease in the freshness of the wine. The electrical circuitry can be configured to operate the gas sensor to generate a second series of gas level measurements. The electrical circuitry can be configured to operate the optical sensor pair to generate a second series of optical transmission measurements. The electrical circuitry can be configured to update the quality parameter for the wine based on both the second series of gas level measurements and the second series of optical transmission measurements.

The housing can include a bore for pouring the wine from the container without removing the housing from the container. The apparatus can include a filter positioned between the gas sensor and the headspace. The filter can shield the gas sensor from water vapor and/or ethanol vapor from the wine. The apparatus can include a liquid resistant membrane for preventing liquid from reaching one or more of the gas sensor, the optical sensor pair, and the electrical circuitry. The housing of the apparatus can seal the opening of the container when attached to the container and can include a port permitting air from outside the container to reach the gas sensor for improving operation of the gas sensor. The apparatus can include a gas circulation device for circulating gases in the headspace. The gas circulation device can include at least one of a fan and a hand pump.

A bottle can have an opening, a neck, and a headspace inside the bottle above the wine remaining in the bottle. A device for monitoring freshness of wine within the opened bottle of wine can include a housing that removably attaches to the neck of the bottle. The housing can include a measurement portion that extends into the neck of the bottle when the device is attached to the bottle. The device can include a printed circuit board including electrical circuitry. The device can include a sulfur dioxide sensor affixed to the measurement portion of the housing. The sulfur dioxide sensor can be positioned in the headspace of the bottle to perform sulfur dioxide level measurements of the headspace when the device is attached to the bottle. The device can include an optical emitter electrically connected to the printed circuit board and positioned to transmit optical energy through at least a portion of the headspace when the device is attached to the bottle. The device can include an optical detector electrically connected to the printed circuit board and positioned to receive at least a portion of the optical energy transmitted from the optical emitter through the headspace. The optical detector can generate electrical signals corresponding to a magnitude of the portion of the optical energy received at the optical detector. The device can include a display element. The electrical circuitry can be adapted to periodically calculate a freshness value for the wine. The freshness value can be based on a current sulfur dioxide level measurement received from the sulfur dioxide sensor and a current electrical output of the optical detector. The electrical circuitry can be adapted to update information displayed on the display element based on the calculated freshness value. The electrical circuitry can be adapted to calculate the freshness value based on one or more of: a past sulfur dioxide level measurement received from the sulfur dioxide sensor, a past electrical output of the optical detector, and a past calculated freshness value. In some examples, the current sulfur dioxide level measurement can be less than about 1.0 ppm when the wine is not fresh, about 1.0-1.5 ppm when the wine is marginally fresh, and greater than 1.5 ppm when the wine is fresh. In other examples, the current sulfur dioxide level measurement is less than about 1.18 ppm when the wine is not fresh, about 1.18-1.75 ppm when the wine is marginally fresh, and greater than 1.75 ppm when the wine is fresh. In still other examples, the current sulfur dioxide level measurement is less than about 0.59 ppm when the wine is not fresh, about 0.59-0.87 ppm when the wine is marginally fresh, and greater than 0.87 ppm when the wine is fresh.

The electrical circuitry can include a computer processor. The device can include a battery for powering the electrical circuitry, the sulfur dioxide sensor, the optical emitter, the optical detector, the computer processor, and the display element. The electrical circuitry can enter a sleep mode between the periodic calculating and updating to extend a life of the battery. The display element can include one or more light emitting diodes, and updating the information can include changing a color displayed on the one or more light emitting diodes.

The device can include a filter positioned in proximity to the sulfur dioxide sensor for reducing a quantity of vapors from the wine from reaching the sulfur dioxide sensor. The device can include a port permitting air from outside the bottle to reach the sulfur dioxide sensor. The device can include a gas circulation element for circulating gases in the headspace.

The sulfur dioxide sensor can include an aqueous solution of sulfuric acid or propylene carbonate, polytetrafluoroethylene, polycarbonate, noryl polymer, carbon, and precious metals.

A method of monitoring freshness of an opened bottle of wine based on measurements made in a headspace of the opened bottle of wine can include measuring sulfur dioxide levels in the headspace of the opened bottle of wine over a period of time, determining optical energy transmission levels through the headspace over a period of time, and calculating a freshness value for the opened bottle of wine based on changes in the measured sulfur dioxide levels and based on changes in the determined optical energy transmission levels over the period of time. Determining the optical energy transmission levels through the headspace can include driving a band-limited optical emitter in the headspace to generate an optical beam directed at an optical detector located in the headspace, where the optical detector generates an electrical signal that is proportional to an amount of optical energy of the optical beam received at the optical detector. The measured sulfur dioxide levels can include an initial sulfur dioxide level associated with the opening of the bottle wine and a current sulfur dioxide level. Calculating the freshness value can include comparing the current sulfur dioxide level to the initial sulfur dioxide level. The optical energy transmission levels can include an initial optical energy transmission level associated with the opening of the bottle wine and a current optical energy transmission level. Calculating the freshness value can include comparing the current optical energy transmission level to the initial optical energy transmission level. The method can include transmitting an electrical signal to a display device to cause the display device to reflect the calculated freshness value. The method can include exposing a device used to measure the sulfur dioxide level to ambient air for a settling period before exposing the device to the headspace to measure the sulfur dioxide levels in the headspace.

The present disclosure introduces a device according to one or more aspects of the present disclosure.

The present disclosure also introduces a method according to one or more aspects of the present disclosure.

The present disclosure also introduces an apparatus according to one or more aspects of the present disclosure.

The present disclosure also introduces a system according to one or more aspects of the present disclosure.

The present disclosure also introduces a kit according to one or more aspects of the present disclosure.

The present disclosure also introduces a beverage diagnostic device according to one or more aspects of the present disclosure.

The present disclosure also introduces a wine container according to one or more aspects of the present disclosure.

The present disclosure also introduces a wine bottle stopper according to one or more aspects of the present disclosure.

The present disclosure also introduces a preservation device according to one or more aspects of the present disclosure.

It is understood that variations may be made in the foregoing without departing from the scope of the disclosure. For example, instead of, or in addition to, wine, the foregoing may be applied to other beverages. In several exemplary embodiments, the elements and teachings of the various illustrative exemplary embodiments may be combined in whole or in part in some or all of the illustrative exemplary embodiments. In addition, one or more of the elements and teachings of the various illustrative exemplary embodiments may be omitted, at least in part, and/or combined, at least in part, with one or more of the other elements and teachings of the various illustrative embodiments.

Although a glass bottle is shown in the figures as an example of a beverage container, it is not limiting. Other suitable containers can include plastic bladders, plastic bottles, and aluminum containers. The devices and method described herein can be modified to accommodate a wide variety of containers.

Any spatial references such as, for example, "upper," "lower," "above," "below," "between," "bottom," "vertical," "horizontal," "angular," "upwards," "downwards," "side-to-side," "left-to-right," "left," "right," "right-to-left," "top-to-bottom," "bottom-to-top," "top," "bottom," "bottom-up," "top-down," etc., are for the purpose of illustration only and do not limit the specific orientation or location of the structure described above.

In several exemplary embodiments, while different steps, processes, and procedures are described as appearing as distinct acts, one or more of the steps, one or more of the processes, and/or one or more of the procedures may also be performed in different orders, simultaneously and/or sequentially. In several exemplary embodiments, the steps, processes, and/or procedures may be merged into one or more steps, processes, and/or procedures. In several exemplary embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

The terms "exemplary," "in one embodiment," "in some embodiments," "in one example," "in other examples," "in some cases," "in other cases," "in some configurations," "in other configurations," and the like, when used in this description means serving as an example, instance, or illustration, and should not necessarily be construed as preferred or advantageous over other exemplary embodiments. The detailed description includes specific details for providing a thorough understanding of the exemplary embodiments of the disclosure. It will be apparent to those skilled in the art that the exemplary embodiments of the disclosure may be practiced without these specific details. In some instances, well-known structures and devices may be shown in block diagram form in order to avoid obscuring the novelty of the exemplary embodiments presented.

Although several exemplary embodiments have been described in detail above, the embodiments described are exemplary only and are not limiting, and those skilled in the art will readily appreciate that many other modifications, changes, and/or substitutions are possible in the exemplary embodiments without materially departing from the novel teachings and advantages of the present disclosure. Accordingly, all such modifications, changes, and/or substitutions are intended to be included within the scope of this disclosure as defined in the following claims. In the claims, means-plus-function clauses, if any, are intended to cover the structures described herein as performing the recited function and not only structural equivalents, but also equivalent structures.

What is claimed is:

1. An apparatus for determining freshness of wine stored in a container, the container having an opening and having a headspace above the wine inside the container, the apparatus comprising:
a housing removably attachable to the container such that the housing spans the opening of the container and seals the opening of the container when the housing is attached to the container;
a gas sensor affixed to the housing such that the gas sensor extends into the headspace of the container above the wine when the housing is attached to the container;
an optical sensor pair comprising an optical emitter and an optical detector, the optical sensor pair positioned such that the optical sensor pair extends into the headspace above the wine when the housing is attached to the container, the optical emitter and optical detector further positioned such that optical energy emitted from the optical emitter is transmitted through at least a portion of the headspace toward the optical detector; and
electrical circuitry contained in the housing and electrically interfaced to the gas sensor and to the optical sensor pair, the electrical circuitry configured to:
operate the gas sensor to generate a series of gas level measurements each indicating a measured level of a gas in the headspace;
operate the optical sensor pair to generate a series of optical transmission measurements each indicating a level of optical transmission of the emitted optical energy through the portion of the headspace; and
determine a quality parameter for the wine, wherein the quality parameter corresponds to the freshness of the wine and is determined based on both the series of gas level measurements and the series of optical transmission measurements.

2. The apparatus of claim 1 further comprising a visual display element, wherein the electrical circuitry is further configured to display the quality parameter for the wine on the visual display element.

3. The apparatus of claim 1 wherein the gas includes sulfur dioxide, the gas sensor includes a sulfur dioxide sensor, and wherein a decreasing amount of the sulfur dioxide in the headspace as indicated by the series of gas level measurements indicates a decrease in the freshness of the wine.

4. The apparatus of claim 1 further comprising a filter positioned between the gas sensor and the headspace, the filter for shielding the gas sensor from water vapor and/or ethanol vapor from the wine.

5. The apparatus of claim 1 further comprising a liquid resistant membrane for preventing liquid from reaching one or more of the gas sensor, the optical sensor pair, and the electrical circuitry.

6. The apparatus of claim 1 wherein the housing seals the opening of the container when attached to the container and includes a port permitting air from outside the container to reach the gas sensor for improving operation of the gas sensor.

7. The apparatus of claim 1 further comprising a gas circulation device for circulating gases in the headspace.

8. The apparatus of claim 7 wherein the gas circulation device includes at least one of a fan and a hand pump.

9. The apparatus of claim 1 wherein the optical emitter includes a light emitting diode (LED).

10. The apparatus of claim 9 wherein the LED has an output wavelength of approximately 428 nm.

11. The apparatus of claim 9 wherein the LED has an output wavelength of approximately 940 nm.

12. The apparatus of claim 1 wherein the electrical circuitry is further configured to:
further operate the gas sensor to generate a second series of gas level measurements;
further operate the optical sensor pair to generate a second series of optical transmission measurements; and
update the quality parameter for the wine based on both the second series of gas level measurements and the second series of optical transmission measurements.

13. The apparatus of claim 1 wherein the housing includes a bore for pouring the wine from the container without removing the housing from the container.

14. A device for monitoring freshness of an opened bottle of wine, the bottle having an opening, a neck, and a headspace inside the bottle above the wine remaining in the bottle, the device comprising:
a housing that removably attaches to the neck of the bottle, the housing including a measurement portion that extends into the neck of the bottle when the device is attached to the bottle;
a printed circuit board including electrical circuitry;
a sulfur dioxide sensor affixed to the measurement portion of the housing, the sulfur dioxide sensor positioned in the headspace of the bottle to perform sulfur dioxide level measurements of the headspace when the device is attached to the bottle;
an optical emitter electrically connected to the printed circuit board and positioned to transmit optical energy through at least a portion of the headspace when the device is attached to the bottle;
an optical detector electrically connected to the printed circuit board and positioned to receive at least a portion of the optical energy transmitted from the optical emitter through the headspace, the optical detector generating electrical signals corresponding to a magnitude of the portion of the optical energy received at the optical detector; and
a display element;
wherein the electrical circuitry is adapted to periodically calculate a freshness value for the wine, the freshness value based on a current sulfur dioxide level measurement received from the sulfur dioxide sensor and a current electrical output of the optical detector, the electrical circuitry further adapted to update information displayed on the display element based on the calculated freshness value.

15. The device of claim 14 wherein the electrical circuitry is further adapted to calculate the freshness value further based on one or more of: a past sulfur dioxide level measurement received from the sulfur dioxide sensor, a past electrical output of the optical detector, and a past calculated freshness value.

16. The device of claim 14 wherein the current sulfur dioxide level measurement is less than about 1.0 ppm when the wine is not fresh, about 1.0-1.5 ppm when the wine is marginally fresh, and greater than 1.5 ppm when the wine is fresh.

17. The device of claim 14 wherein the current sulfur dioxide level measurement is less than about 1.18 ppm when the wine is not fresh, about 1.18-1.75 ppm when the wine is marginally fresh, and greater than 1.75 ppm when the wine is fresh.

18. The device of claim 14 wherein the current sulfur dioxide level measurement is less than about 0.59 ppm when the wine is not fresh, about 0.59-0.87 ppm when the wine is marginally fresh, and greater than 0.87 ppm when the wine is fresh.

19. The device of claim 14 wherein the electrical circuitry includes a computer processor, the device further comprising a battery for powering the electrical circuitry, the sulfur dioxide sensor, the optical emitter, the optical detector, the computer processor, and the display element.

20. The device of claim 14 wherein the electrical circuitry enters a sleep mode between the periodic calculating and updating to extend a life of the battery.

21. The device of claim 14 wherein the display element includes one or more light emitting diodes and updating the information includes changing a color displayed on the one or more light emitting diodes.

22. The device of claim 14 further comprising a filter positioned in proximity to the sulfur dioxide sensor for reducing a quantity of vapors from the wine from reaching the sulfur dioxide sensor.

23. The device of claim 14 further comprising a port permitting air from outside the bottle to reach the sulfur dioxide sensor.

24. The device of claim 14 further comprising a gas circulation element for circulating gases in the headspace.

25. The device of claim 14 wherein the sulfur dioxide sensor contains an aqueous solution of sulfuric acid or propylene carbonate, polytetrafluoroethylene, polycarbonate, noryl polymer, carbon, and precious metals.

* * * * *